(12) United States Patent
Carson et al.

(10) Patent No.: US 6,562,819 B2
(45) Date of Patent: May 13, 2003

(54) COMPOUNDS FOR INHIBITION OF CERAMIDE-MEDIATED SIGNAL TRANSDUCTION

(75) Inventors: Dennis A. Carson, Del Mar, CA (US); Howard Cottam, Fallbrook, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/951,198

(22) Filed: Sep. 13, 2001

(65) Prior Publication Data

US 2002/0165202 A1 Nov. 7, 2002

Related U.S. Application Data

(60) Division of application No. 08/858,778, filed on May 19, 1997, now Pat. No. 6,323,201, and a continuation-in-part of application No. 08/367,102, filed on Dec. 29, 1994, now abandoned, and a continuation-in-part of application No. 08/482,551, filed on Jun. 7, 1995, now Pat. No. 5,843,943.

(51) Int. Cl.[7] ...................... C07D 217/24; A61K 31/47
(52) U.S. Cl. .................... 514/235.2; 514/309; 544/128; 546/141
(58) Field of Search ........................ 546/141; 544/128; 514/235.2, 309

(56) References Cited

U.S. PATENT DOCUMENTS

| | | | | |
|---|---|---|---|---|
| 4,315,855 A | * | 2/1982 | Schefczik | 534/771 |
| 4,593,095 A | | 6/1986 | Snyder et al. | 544/272 |
| 4,766,133 A | | 8/1988 | Fischli et al. | 514/338 |
| 4,769,377 A | | 9/1988 | Snyder et al. | 514/263 |
| 5,162,340 A | * | 11/1992 | Chakravarty et al. | 514/222.5 |
| 5,593,991 A | | 1/1997 | Adams et al. | 514/235.2 |
| 5,670,527 A | | 9/1997 | Adams et al. | 514/341 |
| 5,969,184 A | | 10/1999 | Adams et al. | 564/154 |
| 6,020,356 A | | 2/2000 | Guglielmotti et al. | 514/403 |

FOREIGN PATENT DOCUMENTS

| | | |
|---|---|---|
| EP | 0733633 | 9/1996 |
| JP | 08-092250 | 4/1996 |
| WO | WO 92 21344 A | 12/1992 |
| WO | 92 21344 A | 12/1992 |
| WO | WO 94 22449 A | 10/1994 |
| WO | 94 22449 A | 10/1994 |
| WO | 94/22449 | 10/1994 |
| WO | WO 94 22863 A | 10/1994 |
| WO | 94 22863 A | 10/1994 |
| WO | 94/22863 | 10/1994 |
| WO | 96 20710 A | 7/1996 |
| WO | WO 96 20710 A | 7/1996 |
| WO | WO 98 52948 A | 11/1998 |
| WO | 98 52948 A | 11/1998 |

OTHER PUBLICATIONS

HCAPLUS Bibliographic Database Search Print–out, Chemical Registry No. 172750–90–2, STN International/American Chemical Society, 7 p., (Jun. 21, 2000).

HCAPLUS Bibliographic Database Search Print–out, Chemical Registry No. 165806–09–7, STN International/American Chemical Society, 16 p., (Jun. 21, 2000).

"PTO Examination Guidelines on Utility Requirement", *BNA's Patent, Trademark & Copyright Journal*, vol. 50, 15, (Jul. 20, 1999).

Bruns, R.F., "Adenosine Antagonism by Purines, Pteridines and Benzopteridines in Human Fibroblasts", *Biochemical Pharmacology*, 30, pp. 325–333, (1981).

Chaby, R., "Strategies for the Control of LPS–Mediated Pathophysiological Disorders", *Drug Discovery Today*, 4, 209–221, (May 1999).

Cottam, H.B., "New Adenosine Kinase Inhibitors with Oral Antiinflammatory Activity", *Drugs of The Future 19* (5), pp. 485–491, (1994).

Cottam, H.B., et al., "New Adenosine Kinase Inhibitors with Oral Antiinflammatory Activity: Synthesis and Biological Evaluation", *Journal of Medicinal Chemistry*, 36 (22), pp. 3424–3430, (Oct. 29, 1993).

Leoni, L.M., et al., "Modulation of Ceramide–Activated Protein Phosphatase 2A Activity by Low Molecular Weight Aromatic Compounds", *Biochemical Pharmacology*, 55 (7), pp. 1105–1111, (Apr. 1, 1998).

Opal, S.M., et al., "Clinical Trials for Severe Sepsis", *Infec. Dis. Clinics of North America*, 13, 285–297, (Jun. 1999).

* cited by examiner

*Primary Examiner*—Zinna Northington Davis
(74) *Attorney, Agent, or Firm*—Schwegman, Lundberg, Woessner & Kluth, P.A.

(57) ABSTRACT

Novel, heterocyclic compounds having at least one ring nitrogen, disclosed side chains and, in some embodiments, an oxygen ortho to the ring nitrogen inhibit inflammatory responses associated with TNF-α and fibroblast proliferation in vivo and in vitro. The compounds of the invention neither appreciably inhibit the activity of cAMP phosphodiesterase nor the hydrolysis of phosphatidic acid, and are neither cytotoxic nor cytostatic. Preferred compounds of the invention are esters. Methods for the use of the novel compounds to inhibit ceramide-mediated intracellular responses in stimuli in vivo (particularly TN-α) are also described. The methods are expected to be of use in reducing inflammatory responses (for example, after angioplasty), in limiting fibrosis (for example, of the liver in cirrhosis), in inhibiting cell senescence, cell apoptosis and UV induced cutaneous immune suppression. Compounds having enhanced water solubility are also described.

14 Claims, 14 Drawing Sheets

INHIBITION OF TYPE IU PHOSPHODIESTERASE 36,895-4
3-HYDROXYISOQUINOLINE, 99%
$C_9N_7NO$
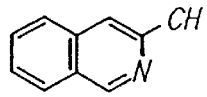
S94,009-7
3-AMINO-4-CYANO-2-HEXYL-7-NITRO-1(2H)-IOSQUINOLONE
$C_{16}H_{18}N_4O_3$
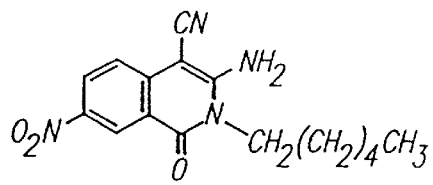
S75,699-7
2-BROMO-4-NITRO-6(5H)-PHENANTHRIDINONE
$C_{13}H_7BrN_2O_3$
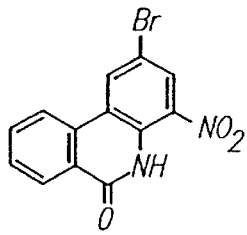
FIG. 14(B)
S52,626-6
6,7-DIMETHOXY-1(2H)-ISOQUINOLONE
$C_{11}H_{11}NO_3$
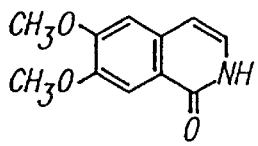
S84,100-5
4-ISOQUINOLINECARBOXYLIC ACID
$C_{10}H_7NO_2$
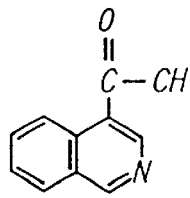
15,013-4
1-ISOQUINOLINECARBOXYLIC ACID, 99%
$C_{10}H_7NO_2$
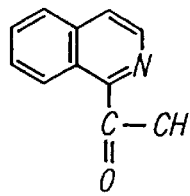

S76,087-0
2-(2-(3,4-DIMETHOXYPHENYL)ETHYL)ISOQUINOLINE-1,3
(2H,4H)-DIONE
$C_{19}H_{19}NO_4$

S76,473-6
1,2-DIHYDRO-2-METHYL-1-OXO-3-ISOQUINOLINES
UTYRIC ACID
$C_{14}H_{15}NO_3$ 29,963-4
5(5H)-PHENANTHRIDINONE
$C_{13}H_9NO$

N165-8
1,8-NAPHTHALIMIDE, 99%
$C_{12}H_7NO_2$ 33,854-0
3-ISOQUINOLINECARBOXYLIC ACID HYDRATE, 99%
$C_{10}H_7NO_2$

COMPOUNDS FOR INHIBITION OF CERAMIDE-MEDIATED SIGNAL TRANSDUCTION

RELATED PATENT APPLICATIONS

This application is a Division of U.S. application Ser. No. 08/858,778 filed May 19, 1997, now U.S. Pat. No. 6,323, 201, issued Nov. 27, 2001, which is hereby incorporated by reference and is a continuation-in-part of U.S. patent application Ser. No. 08/367,102, filed Dec. 29, 1994 and a continuation-in-part of U.S. patent application Ser. No. 08/482,551, filed Jun. 7, 1995 now U.S. Pat. No. 5,843,943.

STATEMENT OF GOVERNMENT SUPPORT

This invention may have been made with government support under Grant No. GM-23200 awarded by the National Institutes of Health. The government may have certain rights in the invention.

BACKGROUND OF THE INVENTION

1. Field of the Invention

The invention relates to compounds effective in modulating cellular responses stimulated by ceramide-mediated signal transduction, in particular in response to stimulus by the cytokine tumor necrosis factor α (TNF-α). More specifically, it relates to compounds which inhibit the development of conditions associated with cell stimulus through the ceramide-mediated signal transduction pathway.

2. History of the Prior Art

The sphingomyelin pathway is a cellular signal transduction pathway that is believed to be involved in mediating cellular responses to several cytokines (including TNF-α and IL-Iβ) and growth factors (e.g., platelet derived growth factor and fibroblast growth factor) (see, e.g., Dressier, et al., Science, 259:1715–1718, 1992; and, Jacobs and Kester, Amer.J.Physiol., 265: 740–747, 1993). It is believed that interaction of such molecules with cell surface receptors triggers activation of a plasma membrane sphingomyelinase. Sphingomyelinase in turn catalyzes the hydrolysis of sphingomyelin to deramide and phosphocholine. Ceramide is believed to act as a second messenger through activation of a proline-directed, serine/threonine kinase (ceramide-activated protein kinase or "CaPK"). Ceramide also interacts with MAP kinase and protein kinase C zeta (see, e.g., Rivas, et al., Blood, 83:2191–2197, 1993) and with a serine/threonine protein phosphatase (see, Hannun, et al., TIBS, 20:73–77, 1995).

Recent investigation has provided evidence that the sphingomyelin pathway may mediate cellular senescence and apoptosis (programmed cell death) in response to TNF-α (see, e.g., Jayadev, et al., J.Biol.Chem., 270:2047–2052, 1994; and, Dbaibo, et al., J.Biol.Chem., 268:17762–17766, 1993) and radiation (Haimovitz-Friedman, et al., J.Exp.Med., 180:525–535, 1994). In this respect, ceramide has been presumed to mimic the effects of TNF-α on intracellular processes.

SUMMARY OF THE INVENTION

The invention is directed toward the development and use of compounds to inhibit cellular responses to ceramide metabolites of the sphingomyelin signal transduction pathway, such as inflammation, fibrosis, ultraviolet light induced cutaneous immune suppression, cell senescence and apoptosis.

In one aspect, the invention consists of novel compounds comprised of heterocyclic molecules with biologically active side chains (the "compounds of the invention"). Purine, pteridine, thiadiazolopyrimidine, quinalozine and isoquinolone based compounds are included in the invention. Particularly preferred among these compounds are those which have enhanced water solubility; e.g., morpholinoethyl esters of the compounds of the invention.

The compounds of the invention do not inhibit the activity of cAMP phosphodiesterase and therefore do not pose the risk of side-effects associated with other TNF-α inhibitors (e.g., pentoxifylline), such as sleeplessness and anxiety. Indeed, surprisingly, one of the more potent TNF-α activity inhibitors among the compounds of the invention (compound 37) had the least inhibitory effect on phosphodiesterase type IV, the predominant phosphodiesterase isoenzyme in monocytes and neutrophils. This is due to the fact that compounds such as 37 do not have a methylxanthine structure. Many common phosphodiesterase inhibitors (such as theophylline, theobromine, and caffeine) are methylxanthine compounds.

Moreover, all of the compounds of the invention inhibit apoptosis and retard cellular responses to TNF-α in vitro and in vivo with greater potency than pentoxifylline. Unexpectedly, the potency of at least the non-isoquinolone compounds appears to be dependent in part on the presence of ring nitrogens (other than the pyrimidine nitrogens), suggesting that binding to the target receptor responsible for inhibition of the activity of TNF-α observed is also regulated to some extent by the presence of such ring nitrogens. Further, the effects of all of the compounds appear to be totally unrelated to phosphodiesterase inhibition. This is particularly interesting given that increases in cAMP levels in cells can induce apoptosis in B cells (see, e.g., Lømo, et al., J.Immunol., 154:1634–1643, 1995).

Recently, studies have shown (see, e.g. Verheij, et al., Nature, 380:75–79, 1996) that ceramide initiates apoptosis through the stress-activated protein kinase (SAPK/JNK) pathway. Thus, cells exposed to stresses such as ionizing radiation, hydrogen peroxide, UV-C radiation, heat shock, and TNF-α, or to C-2 ceramide, acquired biochemical and morphological features typical of apoptosis. Indeed, these stresses have been shown to increase cellular levels of ceramide. Moreover, the role of one of the stress-activated protein kinases, c-jun (referred to as Jun kinase or JNK) in apoptosis was confirmed following stress and C-2 ceramide exposure. In this regard, compounds of the invention, particularly the isoquinolines, have shown activity as inhibitors of Jun kinase activation induced by anisomycin (a nonspecific protein synthesis inhibitor) in MOLT-4 human lymphoblastoid cells or by LPS in RAW mouse macrophages. Therefore, a possible mechanism of activity of these compounds is the inhibition of one arm of the stress response pathway involving a Jun kinase in response to stress or to ceramide.

Another aspect of the invention consists of methods for the use of the novel compounds in inhibiting ceramide-activated cellular responses to stimuli, in particular stimuli for cell senescence and apoptosis. This aspect of the invention has potential therapeutic significance in the treatment of cell death associated conditions such as stroke, cardiac ischemia, nerve damage and Alzheimer's disease.

Another aspect of the invention consists of methods which exploit the ability of the compounds of the invention to absorb UW radiation. This aspect of the invention has potential therapeutic significance in the treatment and prevention of radiation dermatoses, including those associated with therapeutic regimes for treatment of cancer.

The compounds of the invention are expected to be particularly useful in reducing the effects of aging in skin as well as the onset and progression of radiation dermatitis.

In another aspect, the invention features a compound having the formula:

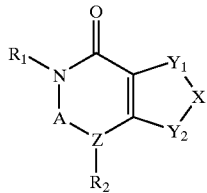

where $R_1$ is a terminally substituted normal alkyl having from 1 to 7 carbon atoms, a terminally substituted alkenyl having from 2 to 7 carbon atoms, a terminally substituted ether having from 2 to 6 carbon atoms, a terminally substituted secondary amine having from 2 to 6 carbon atoms, or substituted aryl having less than 8 carbons, where said terminal group is $NH_2$, substituted amino, acyloxy, $SO_3H$, $PO_4H_2$, NNO(OH), $SO_2NH_2$, $PO(OH)NH_2$, $SO_2R$ or COOR, where R is H, an alkyl having from 1 to 4 carbon atoms, an alkenyl having from 1 to 4 carbon atoms, tetrazolyl, benzyl, or an alkylamino, where the alkyl group has from 1 to 4 carbon atoms and the amino is $NH_2$ or a substituted amino where the substituents on the amino have 1 to 6 carbon atoms, one of which can be replaced by an oxygen atom or nitrogen atom;

Z is C, CH, or N;

$R_2$ is an alkyl, a cyclic alkyl, a heterocyclic alkyl, alkenyl, or aralkyl having less than 7 carbon atoms when Z is C, $R_2$ is a halogen, NO, amino, or substituted amino when Z is CH, or $R_2$ is H, an alkyl, a cyclic alkyl, a heterocyclic alkyl, alkenyl, or aralkyl having less than 7 carbon atoms when Z is N;

A is CO when Z is N, or $CR_5$ when Z is C or CH, where $R_5$ is H, an alkyl, a cyclic alkyl, a heterocyclic alkyl, alkenyl, aryl or aralkyl having less than 7 carbon atoms, OH, or an O-alkyl having from 1 to 5 carbon atoms and there is a double bond between Z and A when Z is C and a single bond between Z and A when Z is CH;

$Y_1$ is N, $NR_6$, or $CR_6$, where $R_6$ is H, NO, an amino, a substituted amino, an alkyl, a cyclic alkyl, a heterocyclic alkyl, alkenyl, or aralkyl having less than 7 carbon atoms;

$Y_2$ is N or CH; and

X is S when $Y_1$ and $Y_2$ are N, $CR_7$ when $Y_1$ is $NR_6$ where $R_7$ is H, OH, SH, Br, Cl, or I, or =$C(R_3)$—$C(R_4)$= when $Y_1$ is N, CH or $CR_6$ and $Y_2$ is N or CH, where each of $R_3$ and $R_4$, independently, is H, an alkyl, a cyclic alkyl, a heterocyclic alkyl, alkenyl, aryl, alkylcarboxyl, or aralkyl having less than 7 carbon atoms, SH, OH or an O-alkyl having from 1 to 5 carbon atoms, or a salt thereof.

In another aspect, the invention features a compound having the formula:

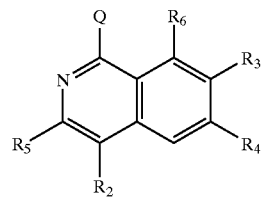

where Q is a halogen or substituted amino, $R_2$ is a halogen, NO, an amino, or a substituted amino, $R_3$ is SH or OH, $R_4$ is SH or OH, R, is H, an alkyl, a cyclic alkyl, a heterocyclic alkyl, alkenyl, aryl or aralkyl having less than 7 carbon atoms, OH, or an O-alkyl having from 1 to 5 carbon atoms, and $R_6$ is NO, an amino, or a substituted amino, or a salt thereof.

In preferred embodiments, the compound has the formula:

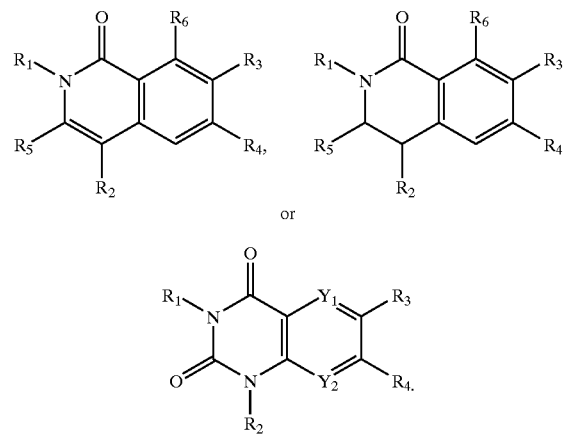

Preferably, $R_1$ is a terminally substituted normal alkyl having from 1 to 7 carbon atoms, where said terminal group and is $NH_2$, substituted amino, or COOR, where R is H, an alkyl having from 1 to 4 carbon atoms, or an alkylamino, where the alkyl group has from 1 to 4 carbon atoms and the amino is a substituted amino where the substituents on the amino have 1 to 6 carbon atoms, one of which can be replaced by an oxygen atom or nitrogen atom; $R_2$, when present, is an alkyl having less than 7 carbon atoms (i.e., Me, or —$(CH_2)_2CH_3$); each of $R_3$ and $R_4$, independently, is H, SH, OH, an alkyl, aryl, alkylcarboxyl, or aralkyl having less than 7 carbon atoms, or an O-alkyl having from 1 to 5 carbon atoms; and $R_6$ is NO, an amino, or a substituted amino (i.e., NHR, or $NR_2$, where R is H, an alkyl having from 1 to 4 carbon atoms, an alkenyl having from 1 to 4 carbon atoms, tetrazolyl, benzyl, an alkylamino, where the alkyl group has from 1 to 4 carbon atoms and the amino is $NH_2$ or a substituted amino where the substituents on the amino have 1 to 6 carbon atoms, one of which can be replaced by an oxygen atom or nitrogen atom, aryl, or substituted aryl, where the substituted aryl has one, two, or three substituents including halogens or alkyls having 1 to 4 carbons). More preferably, $R_1$ is a terminally substituted normal alkyl having from 1 to 4 carbon atoms where said terminal group is COOR where R is an N-morpholinoalkyl group (i.e., an N-morpholinoethyl group), and each of $R_3$ and $R_4$, independently, is an O-alkyl having from 1 to 5 carbon atoms.

Most preferably, $R_1$ is —$(CH_2)_3COOR$ where R is an N-morpholinoethyl group, and $R_3$ and $R_4$ each are H or methoxy groups, thus providing the compounds with enhanced water solubility.

In other preferred embodiments, the compound has the formula:

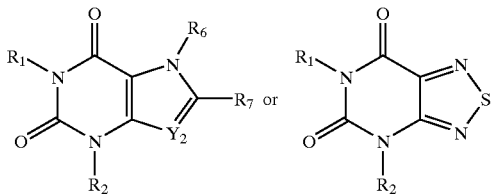

where
R$_1$ is a terminally substituted normal alkyl having from 1 to 7 carbon atoms, a terminally substituted alkenyl having from 2 to 7 carbon atoms, a terminally substituted ether having from 2 to 6 carbon atoms, a terminally substituted secondary amine having from 2 to 6 carbon atoms, or substituted aryl having less than 8 carbons, where said terminal group is NH$_2$, substituted amino, acyloxy, SO$_3$H, PO$_4$H$_2$, NNO(OH), SO$_2$NH$_2$, PO(OH)NH$_2$, SO$_2$R or COOR, where R is H, an alkyl having from 1 to 4 carbon atoms, an alkenyl having from 1 to 4 carbon atoms, tetrazolyl, benzyl, or an alkylamino, where the alkyl group has from 1 to 4 carbon atoms and the amino is NH$_2$ or a substituted amino where the substituents on the amino have 1 to 6 carbon atoms, one of which can be replaced by an oxygen atom or nitrogen atom;

R$_2$ is H, an alkyl, a cyclic alkyl, a heterocyclic alkyl, alkenyl, or aralkyl having less than 7 carbon atoms;

Y$_2$ is N or CH;

R$_6$ is H, an alkyl, a cyclic alkyl, a heterocyclic alkyl, alkenyl, or aralkyl having less than 7 carbon atoms; and R$_7$ is H, OH, SH, Br, Cl, or I, or a salt thereof.

Further advantages and embodiments of the invention included therein will become apparent from the following disclosure.

BRIEF DESCRIPTION OF THE DRAWINGS

FIGS. 14(a) through (c) show the structure of commercially available isoquinoline structures whose inhibitory effect with respect to production of TNF-α by human monocytes prior to modification to add side chain substituents according to the invention was tested. Except for Compound S52, 626-6 (6,7-dimethoxy-1(2H)-isoquinoline, which possessed mild inhibitory activity as shown in FIG. 10) none of the tested compounds possessed any such inhibitory activity prior to their modification according to the invention, even at concentrations up to 500 μM.

DESCRIPTION OF THE PREFERRED EMBODIMENTS

I. Compounds of the Invention

Figure 1:
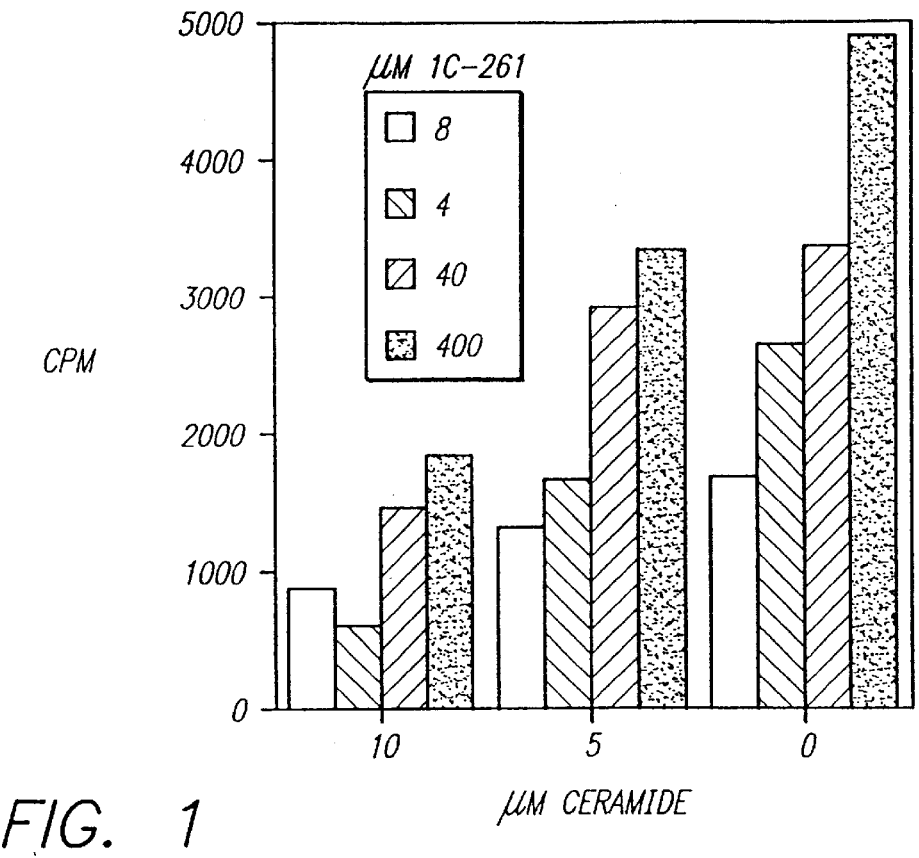
FIG. 1 is a bar graph depicting inhibition of cell growth arrest in 3T3 fibroblasts according to the invention after growth arrest was induced through deprivation of the cells of serum. The cells were incubated and grown to 90% confluence in serum. The medium was then removed and replaced with serum-free medium. To assess the effect of an inventive compound (no. 37, a pteridine) on cell senescence in the presence of ceramide, aliquots of the cells were incubated with different concentrations of each. Concentrations of compound no. 37 are indicated by the insert legend while concentrations of ceramide are indicated along the x axis. Inhibitory effects were assessed as a measure of DNA synthesis; [$^3$H] thymidine incorporation detection is indicated along the y axis.

The compounds of the invention generally comprise purines, pteridines, thiadiazolopyrimidines and quinazolines prepared according to the schemes described below. For reference, the techniques used in synthesizing the compounds are adaptations of the well-known Traube Synthesis protocol (Lister, "*Purines*" (Wiley-Interscience, 1971), at p. 220), beginning with 4,5-diaminopyrimidines; to wit: (1) for the purines in general, see Brown, "*The Chemistry of Heterocyclic Compounds: Fused Pyrimidines*", Part II, The Purines, 1971), at pp. 31–90; (2) for the 9-dieazapurines in particular, see Fox, et al., *J. Org. Chem.*, 43:2536, 1978; (3) for the pteridines, see, for a description of the standard Timmis reaction, Nishigaki, et al., *Heterocycles*, 15:757–759, 1981; Timmis, *Nature*, 164:13 9, 1949, (or other standard Traube-like protocols for preparing pteridines by ring closure of diaminopyfimidines using a two carbon reagent); and, (4) for the pyrimidines, see, Schrage and Hitchings, *J. Org. Chem.*, 16:207, 1951.

Compounds of the invention, intermediates and compounds tested for comparison of activity to the compounds of the invention are identified in the discussion below by the numbers assigned to each compound in Table 1.

TABLE I

Physicochemical Data for all New Compounds and TNF-α Inhibition Data

| Comp | Type | | mp (° C.) | formula | analyses[a] | TNFαIC$_{50}$[b] |
|------|------|---|-----------|---------|-------------|------------------|
| 1 | I | 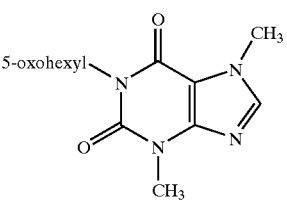 | 102–103 | | | 85 |
| 2 | I | 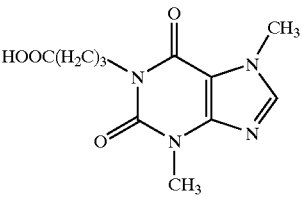 | 208–210 | | | >200 |

TABLE I-continued

Physicochemical Data for all New Compounds and TNF-α Inhibition Data

| Comp | Type | Structure | mp (° C.) | formula | analyses[a] | TNFαIC$_{50}$[b] |
|---|---|---|---|---|---|---|
| 4 | I | EtOOCH$_2$C-substituted 1,3,7-trimethylxanthine | 162–165 | $C_{11}H_{14}N_4O_4$ | C, H, N | 200 |
| 5 | I | EtOOC(H$_2$C)$_2$-substituted | 76–78 | $C_{12}H_{16}N_4O_4$ | HRMS | 10 |
| 6 | I | EtOOC(H$_2$C)$_3$-substituted | 73–75 | $C_{13}H_{18}N_4O_4$ | C, H, N | 6 |
| 7 | I | EtOOC(H$_2$C)$_4$-substituted | 84–85 | $C_{14}H_{20}N_4O_4$ | C, H, N | 11 |
| 8 | I | MeOOCPhH$_2$C-substituted | 158–160 | $C_{16}H_{16}N_4O_4$ | C, H, N | >200 |
| 10 | I | EtOOC(H$_2$C)$_3$-substituted, 8-Br | 101–102 | $C_{13}H_{17}BrN_4O_4$ | C, H, N | 60 |
| 11 | I | MeOOCPhH$_2$C-substituted, 8-Br | 218–219 | $C_{16}H_{15}BrN_4O_4$ | C, H, N | >200 |

TABLE I-continued
Physicochemical Data for all New Compounds and TNF-α Inhibition Data
| Comp | Type | Structure | mp (° C.) | formula | analyses[a] | TNFαIC$_{50}$[b] |
|---|---|---|---|---|---|---|
| 12 | I | 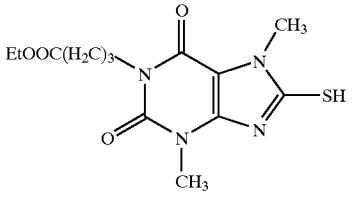 | 202–206 | C$_{13}$H$_{18}$N$_4$O$_4$S | C, H, N | 100 |
| 13 | I | 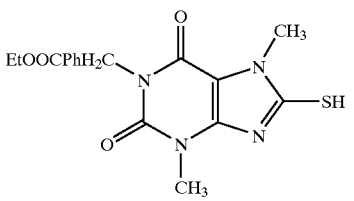 | >293 dec | C$_{17}$H$_{18}$N$_4$O$_4$S | C, H, N | >200 |
| 20 | V | 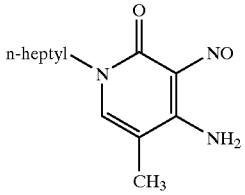 | >218 dec | C$_{12}$H$_{20}$N$_4$O$_3$ | C, H, N | ND[c] |
| 24 | I | 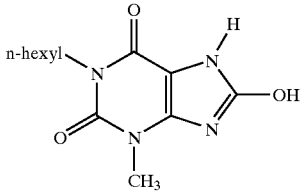 | >295 dec | C$_{12}$H$_{18}$N$_4$O$_3$ | C, H, N | 50 |
| 25 | I | 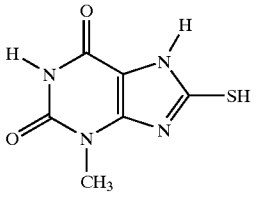 | >320 | | | >200 |
| 31 | I | 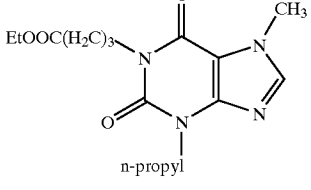 | oil | C$_{15}$H$_{22}$N$_4$O$_4$ | C, H, N | 5 |
| 33 | V | 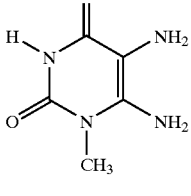 | >270 dec | C$_5$H$_8$N$_4$O$_2$ | C, H, N | ND |

TABLE I-continued

Physicochemical Data for all New Compounds and TNF-α Inhibition Data

| Comp | Type | Structure | mp (° C.) | formula | analyses[a] | TNFαIC$_{50}$[b] |
|---|---|---|---|---|---|---|
| 34 | II | (structure: 3-H, 1-CH$_3$ pteridine-2,4-dione) | 287–289 | $C_7H_6N_4O_2$ | C, H, N | ND |
| 35 | II | (structure: 3-H, 1-n-propyl pteridine-2,4-dione) | 187–189 | $C_9H_{10}N_4O_4$ | C, H, N | ND |
| 36 | II | (structure: 3-EtOOC(H$_2$C)$_3$, 1-CH$_3$) | 90–92 | $C_{13}H_{16}N_4O_4$ | C, H, N | 12 |
| 36a | II | (structure: 3-HOOC(H$_2$C)$_3$, 1-CH$_3$) | 199–202 | $C_{11}H_{12}N_4O_4$ | C, H, N | >200 |
| 37 | II | (structure: 3-EtOOC(H$_2$C)$_3$, 1-n-propyl) | 53–55 | $C_{15}H_{20}N_4O_4$ | C, H, N | 5 |
| 37a | II | (structure: 3-HOOC(H$_2$C)$_3$, 1-n-propyl) | 97–99 | $C_{13}H_{16}N_4O_4$ | C, H, N | >200 |
| 38 | II | (structure: 3-MeOOCHC=HCH$_2$C, 1-CH$_3$) | 118–119 | $C_{12}H_{12}N_4O_4$ | HRMS | 25 |

TABLE I-continued

Physicochemical Data for all New Compounds and TNF-α Inhibition Data

| Comp | Type | structure | mp (° C.) | formula | analyses[a] | TNFαIC$_{50}$[b] |
|---|---|---|---|---|---|---|
| 39 | II | n-hexyl, COOMe, COOMe, CH$_3$ substituted pteridine-2,4-dione | 92–95 | $C_{17}H_{22}N_4O_6$ | C, H, N | ND |
| 40 | II | H, Et, Et, CH$_3$ substituted pteridine-2,4-dione | 218–222 | $C_{11}H_{14}N_4O_2$ | C, H, N | ND |
| 41 | II | EtOOC(H$_2$C)$_3$, Et, Et, CH$_3$ substituted pteridine-2,4-dione | 66–68 | $C_{17}H_{24}N_4O_4$ | C, H, N | 130 |
| 41a | II | HOOC(H$_2$C)$_3$, Et, Et, CH$_3$ substituted pteridine-2,4-dione | 161–162 | $C_{15}H_{20}N_4O_4$ | C, H, N | ND |
| 42 | II | H, Ph, CH$_3$ substituted pteridine-2,4-dione | >307 dec | $C_{13}H_{10}N_4O_4$ | N/A | ND |
| 43a | II | EtOOC(H$_2$C)$_3$, n-butyl substituted pteridine-2,4-dione | N/A | N/A | N/A | N/A |
| 43b | II | EtOOC(H$_2$C)$_3$, n-pentyl substituted pteridine-2,4-dione | N/A | N/A | N/A | N/A |

TABLE I-continued

Physicochemical Data for all New Compounds and TNF-α Inhibition Data

| Comp | Type | Structure | mp (° C.) | formula | analyses[a] | TNFαIC$_{50}$[b] |
|---|---|---|---|---|---|---|
| 43c | II | EtOOC(H$_2$C)$_3$-N, isobutyl (pteridine-2,4-dione) | N/A | N/A | N/A | N/A |
| 43d | II | EtOOC(H$_2$C)$_3$-N, tetrahydrofuturyl | N/A | N/A | N/A | N/A |
| 43e | II | EtOOC(H$_2$C)$_3$-N, benzyl | N/A | N/A | HRMS | N/A |
| 43 | II | EtOOC(H$_2$C)$_3$-N, CH$_3$, Ph | 99–100 | C$_{19}$H$_{20}$N$_4$O$_4$ | HRMS | >200 |
| 44 | III | n-heptyl, CH$_3$ (thiadiazolopyrimidinedione) | 73–75 | C$_{12}$H$_{18}$N$_4$O$_2$S | C, H, N | 75 |
| 45 | III | H, CH$_3$ | 210–213 | C$_5$H$_4$N$_4$O$_2$S | C, H, N | ND |
| 46 | III | H, n-propyl | 142–144 | C$_7$H$_8$N$_4$O$_2$S | C, H, N | ND |

TABLE I-continued

Physicochemical Data for all New Compounds and TNF-α Inhibition Data

| Comp | Type | Structure | mp (° C.) | formula | analyses[a] | TNFαIC$_{50}$[b] |
|---|---|---|---|---|---|---|
| 47 | III | EtOOC(H$_2$C)$_3$-[thiadiazolopyrimidine]-CH$_3$ | 45–47 | C$_{11}$H$_{14}$N$_4$O$_4$S | C, H, N | 25 |
| 47a | III | HOOC(H$_2$C)$_3$-[thiadiazolopyrimidine]-CH$_3$ | 121–122 | C$_9$H$_{10}$N$_4$O$_4$S | HRMS | >200 |
| 48 | III | EtOOC(H$_2$C)$_3$-[thiadiazolopyrimidine]-n-propyl | oil | C$_{13}$H$_{18}$N$_2$O$_3$ | C, H, N | 18 |
| 51 | IV | EtOOC(H$_2$C)$_3$-NH-C(O)-C$_6$H$_4$-NHCH$_3$ | oil | C$_{14}$H$_{20}$N$_4$O$_3$ | C, H, N[f] | ND |
| 52 | IV | EtOOC(H$_2$C)$_3$-[quinazoline]-CH$_3$ | oil | C$_{15}$H$_{18}$N$_2$O$_4$ | C, H, N[g] | 55 |
| 52a | IV | HOOC(H$_2$C)$_3$-[quinazoline]-CH$_3$ | 163–165 | C$_{13}$H$_{14}$N$_2$O$_4$ | C, H, N | >200 |

[a] All compounds analyzed for C, H, N or by exact mass high resolution mass spectrometry; results were within ±0.4% of theoretical values.
[b] Concentration of compound in μM which inhibited the product of TNFα by 50% of control.
[c] ND = not determined.
[d] C: calc'd, 58.61; found 59.22.
[e] H: calc'd, 4.13; found 3.70.
[f] N: calc'd, 10.25; found 9.77.
[g] C: calc'd, 59.62; found, 60.61.
Compound types are: I = purines; II = pteridines; III = thiadiazolopyrimidines; IV = quinazolines; and, V = isoquinolones.
"N/A" means data not available (but can be obtained through conventional analysis techniques).

B. Purine Synthesis

The purines of the invention have the general formula (I):

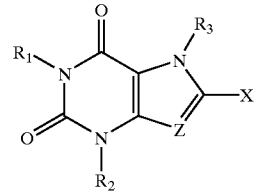

where

Z is N or CH;

$R_1$ is $(CH_2)_nA$, where:

A is $NH_2$, acyloxy, $SO_3H$, $PO_4H_2$, $NNO(OH)$, $SO_2NH_2$, $PO(OH)NH_2$, $SO_2R$, or COOR where R is H, an alkyl having from 1 to 4 carbon atoms, an alkenyl having from 1 to 4 carbon atoms, tetrazolyl or benzyl;

n is any number of atoms from 1 to 7 having saturated and/or unsaturated carbon to carbon bonds, which atoms may include an oxygen or nitrogen atom in place of a carbon atom to form, respectively, ether or amino linkages;

and, preferably, $R_1$ is a ω-carboxyalkyl, ω-carboxyalkenyl, or ω-carboxyaryl having from 1 to 8 carbon atoms, wherein the aromatic group further has as a substituent A (as defined above);

$R_2$ is H, an alkyl (including aliphatic and alicyclic, and heteroalicyclic forms), alkenyl, aralkyl having 1 to 7 carbon atoms or a ω-hydroxyalkyl having from 1 to 7 carbon atoms;

$R_3$ is the same as $R_2$; and

X is H, any halogen, OH, SH, OR', or SR', where R' is an alkyl, alkenyl, phenyl or benzyl having from 1 to 4 carbon atoms.

These compounds are synthesized per the below synthesis scheme (as described in further detail in the Examples).

SCHEME I
(PURINES)

Three basic synthesis protocols were utilized in Scheme I; to wit:

Method A

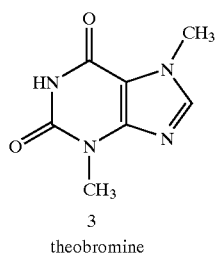 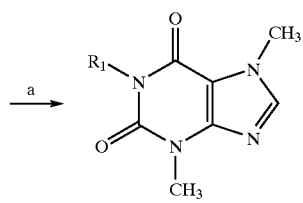

3
theobromine

4, $R_2$ = $CH_2COOEt$
5, $R_2$ = $(CH_2)_2COOEt$
6, $R_2$ = $(CH_2)_3COOEt$
2, $R_2$ = $(CH_2)_3COOH$
7, $R_2$ = $(CH_2)_4COOEt$
8, $R_2$ = $CH_2PhCOOMe$ (para)

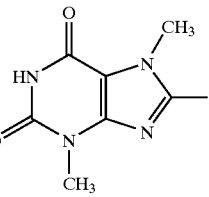 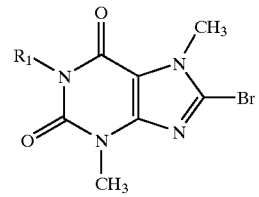

9

10, $R_2$ = $(CH_2)_3COOEt$
11, $R_2$ = $CH_2PhCOOMe$ (para)

(a) $R_1X$, DMF, $K_2CO_3$
(b) $Br_2$, $Ac_2O$
(c) NaSH, EtOH

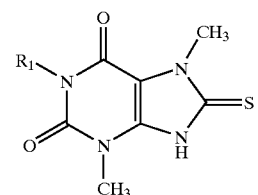

12, $R_2$ = $(CH_2)_3COOEt$
13, $R_2$ = $CH_2PhCOOMe$

Generally, theobromine was used as the starting material under conditions to ensure N-1 alkylation took place in lieu of O-6 alkylation. Compounds 4 through 8, 10 and 11 (Table I) were prepared by this method. Compounds 10 and 11 in particular were prepared by a variation of the alkylation method in which theobromine was first brominated to give 8-bromotheobromine (compound 9), then alkylated. The 8-bromo substituent was also displaced by NaSH to yield the corresponding 8-thioxo derivatives, compounds 12 and 13.

Method B

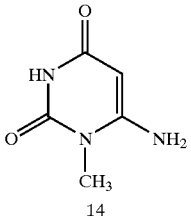 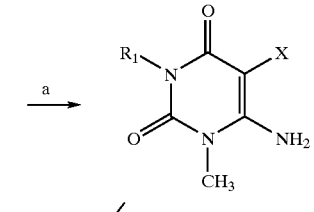

14 b, c

| X | $R_1$ |
|---|---|
| 15, H | n-propyl |
| 16, H | n-hexyl |
| 17, H | n-heptyl |
| 18, N=O | n-propyl |
| 19, N=O | n-hexyl |
| 20, N=O | n-heptyl |

22

-continued

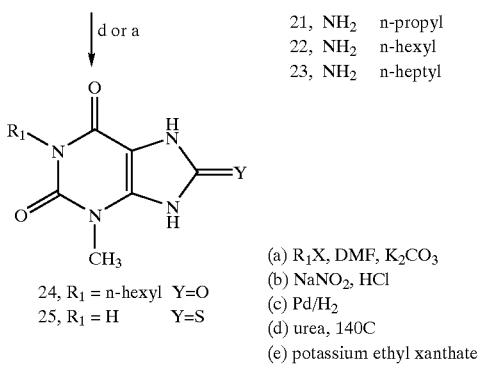

21, NH₂  n-propyl
22, NH₂  n-hexyl
23, NH₂  n-heptyl

24, R₁ = n-hexyl  Y=O
25, R₁ = H        Y=S (a) R₁X, DMF, K₂CO₃
(b) NaNO₂, HCl
(c) Pd/H₂
(d) urea, 140C
(e) potassium ethyl xanthate This method is essentially based on the Traube purine synthesis protocol referred to supra. The method was used to prepare 1,3,8-trisubstituted xanthines bearing no alkyl group at the N-7 position. In this procedure, the N-1 substituted pyrimidine was alkylated at position N-3. Formation of the purine ring was complete by nitrosation, reduction of the nitroso to the amine by catalytic hydrogenation, then ring closure using urea or potassium ethyl xanthate to provide compounds 24 and 25 (respectively, 8-oxo and 8-thioxo derivatives). A detailed description of this protocol is provided in the Examples.

Method C

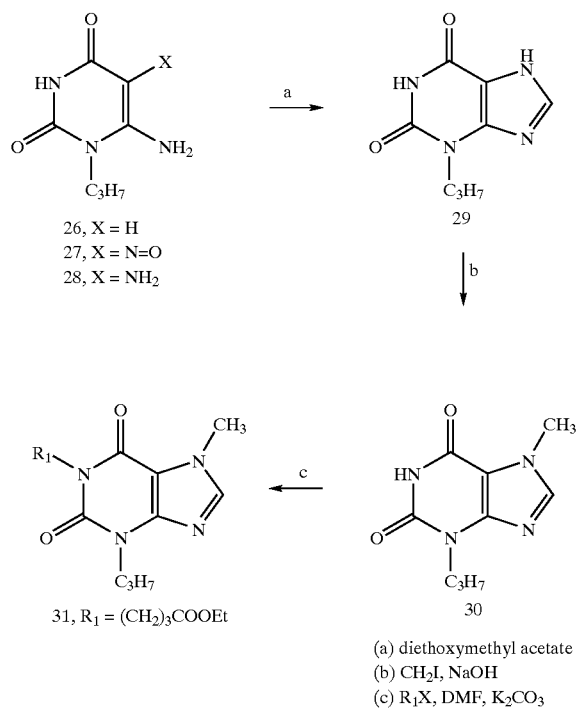

26, X = H
27, X = N=O
28, X = NH₂

29

31, R₁ = (CH₂)₃COOEt

30

(a) diethoxymethyl acetate
(b) CH₃I, NaOH
(c) R₁X, DMF, K₂CO₃

This method was utilized to prepare the N-3 propylpurines. The starting material used was n-propyl urea condensed with ethyl cyanoacetate in the presence of sodium ethoxide to yield the 6-amino-1-propylpyrimidinedione in moderate yield. Commercially available 3-n-propylxanthine could also be used as the starting material.

Ring closure was accomplished as described in method A, except that diethoxymethyl acetate was used as the source of carbon in the ring closure step. Sequential alkylations were then performed using alkyl halides to yield the final compound 31 (ethyl 4-(2,3,6,7-tetrahydro-2,6-dioxo-7-methyl-3-n-propyl-1H-purin-1-yl)butonoic acid). A detailed description of this protocol is provided in the Examples.

C. Pteridine Synthesis

The pteridines of the invention have the general formula (II):

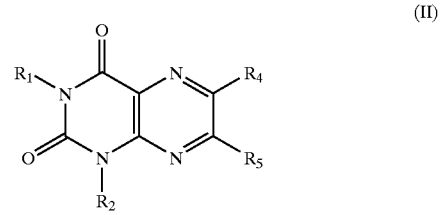

(II)

$R_1$ is $(CH_2)_nA$, where:

A is $NH_2$, acyloxy, $SO_3H$, $PO_4H_2$, $NNO(OH)$, $SO_2NH_2$, $PO(OH)NH_2$, $SO_2R$, or $COOR$ where R is H, an alkyl having from 1 to 4 carbon atoms, an alkenyl having from 1 to 4 carbon atoms, tetrazolyl or benzyl;

n is any number of atoms from 1 to 7 having saturated and/or unsaturated carbon to carbon bonds, which atoms may include an oxygen or nitrogen atom in place of a carbon atom to form, respectively, ether or amino linkages;

and, preferably, $R_1$ is a ω-carboxyalkyl, ω-carboxyalkenyl, or ω-carboxyaryl having from 1 to 8 carbon atoms, wherein the aromatic group further has as a substituent A (as defined above);

$R_2$ is H, an alkyl (including aliphatic and alicyclic, and heteroalicyclic forms), alkenyl, aralkyl having 1 to 7 carbon atoms or a ω-hydroxyalkyl having from 1 to 7 carbon atoms;

$R_4$ is the same as $R_2$, OH or an O-alkyl having from 1 to 5 carbon atoms;

$R_5$ is the same as $R_2$, OH or an O-alkyl having from 1 to 5 carbon atoms; and, Z is N or CH.

These compounds are-synthesized per the below synthesis scheme (which is described in further detail in the Examples.)

SCHEME II
(PTERIDINES)

Method C (above) was chosen as a convenient method to produce N-alkyls in preference to O-alkyls in this group. Method C was modified to this e n as follows:

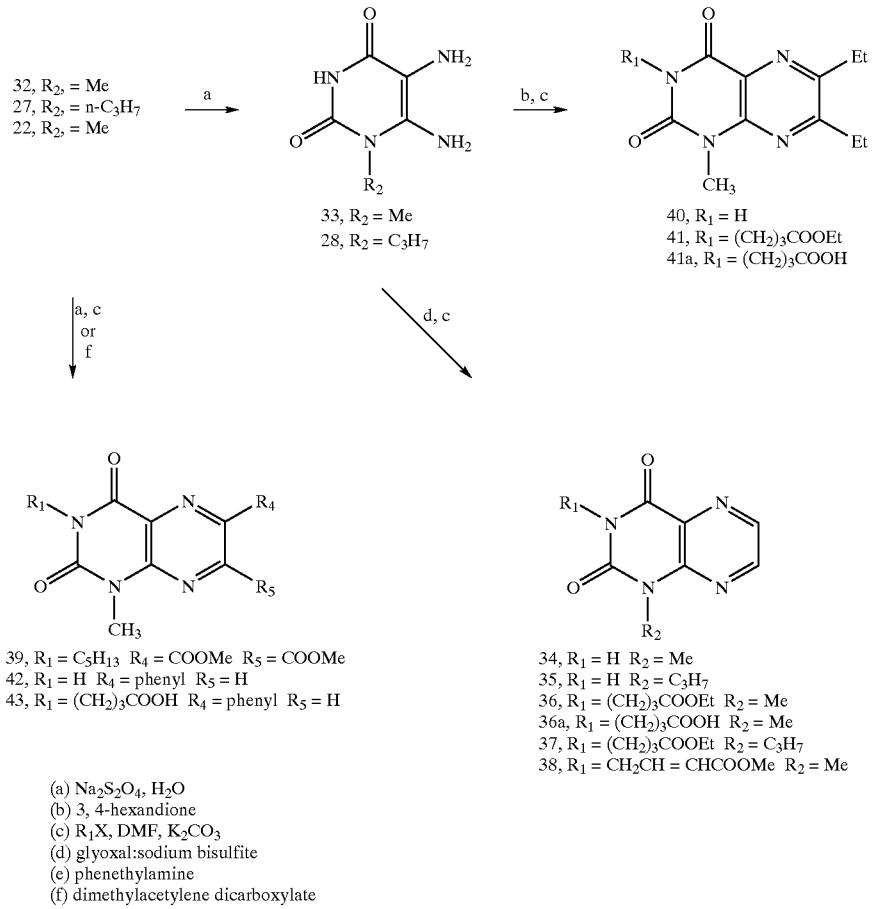

32, $R_2$ = Me
27, $R_2$ = n-$C_3H_7$
22, $R_2$ = Me

33, $R_2$ = Me
28, $R_2$ = $C_3H_7$

40, $R_1$ = H
41, $R_1$ = $(CH_2)_3COOEt$
41a, $R_1$ = $(CH_2)_3COOH$

39, $R_1$ = $C_5H_{13}$  $R_4$ = COOMe  $R_5$ = COOMe
42, $R_1$ = H  $R_4$ = phenyl  $R_5$ = H
43, $R_1$ = $(CH_2)_3COOH$  $R_4$ = phenyl  $R_5$ = H 34, $R_1$ = H  $R_2$ = Me
35, $R_1$ = H  $R_2$ = $C_3H_7$
36, $R_1$ = $(CH_2)_3COOEt$  $R_2$ = Me
36a, $R_1$ = $(CH_2)_3COOH$  $R_2$ = Me
37, $R_1$ = $(CH_2)_3COOEt$  $R_2$ = $C_3H_7$
38, $R_1$ = $CH_2CH=CHCOOMe$  $R_2$ = Me (a) $Na_2S_2O_4$, $H_2O$
(b) 3, 4-hexandione
(c) $R_1X$, DMF, $K_2CO_3$
(d) glyoxal:sodium bisulfite
(e) phenethylamine
(f) dimethylacetylene dicarboxylate Synthesis of the pteridines was based on orthodiaminopyrimidines as precursors. Ring closure fo the orthodiamines (compounds 33 and 28) was accomplished with a two carbon source (e.g., glyoxal) to produce compounds 34 and 35 (N-1 substituted pteridines). Alkylation at N-3 as described with respect to Method A produced the desired pteridines (compounds 36–38). Further, use of 3,4-hexanedione in the ring closure step produced a more lipophilic derivative (compound 41; 6,7-diethyl pteridine). Condensation of compound 22 with dimethylacetylene dicarboxylate formed compound 39 (1,3-dialkylpteridine), while treatment of compound 27 phenethyl amine followed by alkylation provided compound 43 (6-phenyl dialkyl pteridine). Both of the latter protocols utilized a Timmis reaction to produce the desired products. A detailed description of these protocols is provided in the Examples.

D. Thiadiazolopyrimidine Synthesis

The thiadiazolopyrimidines of the invention have the general formula (III):

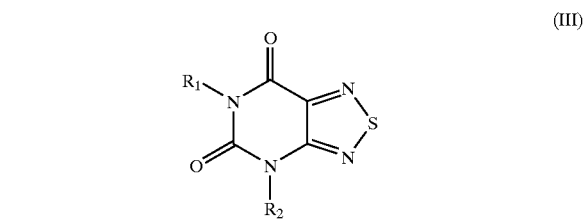

(III)

$R_1$ is $(CH_2)_nA$, where:
  A is $NH_2$, acyloxy, $SO_3H$, $PO_4H_2$, NNO(OH), $SO_2NH_2$, $PO(OH)NH_2$, $SO_2R$, or COOR where R is H, an alkyl having from 1 to 4 carbon atoms, an alkenyl having from 1 to 4 carbon atoms, tetrazolyl or benzyl;
  n is any number of atoms from 1 to 7 having saturated and/or unsaturated carbon to carbon bonds, which atoms may include an oxygen or nitrogen atom in place of a carbon atom to form, respectively, ether or amino linkages; and
  and, preferably, $R_1$ is a ω-carboxyalkyl, ω-carboxyalkenyl, or ω-carboxyaryl having from 1 to 8 carbon atoms, wherein the aromatic group further has as a substituent A (as defined above); and $R_2$ is H, an alkyl (including aliphatic and alicyclic, and heteroalicyclic forms), alkenyl, aralkyl having 1 to 7 carbon atoms or a ω-hydroxyalkyl having from 1 to 7 carbon atoms.

These compounds are synthesized per the below synthesis scheme (as described in further detail in the Examples).

SCHEME III (THIADIAZOLOPYRIMIDINES)

Method C (above) was chosen as a convenient method to produce N-alkyls in preference to O-alkyls in this group. Method C was modified to this end as follows:

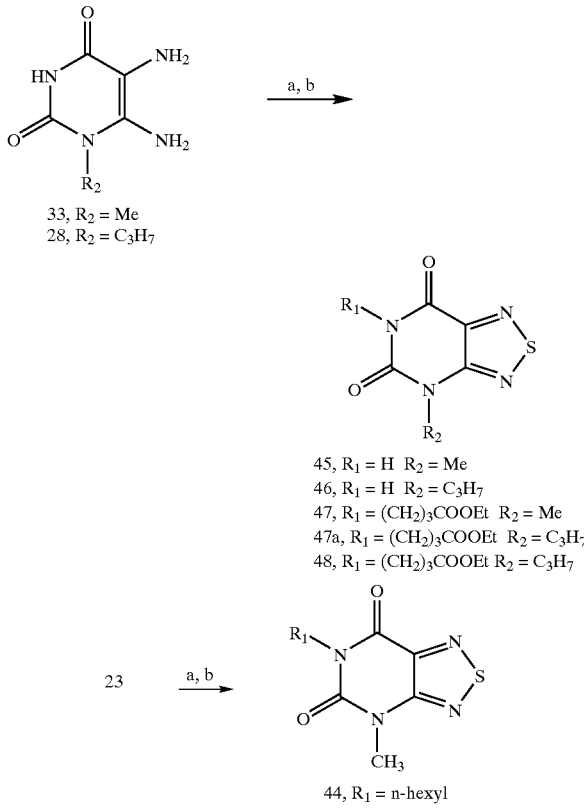

33, $R_2$ = Me
28, $R_2$ = $C_3H_7$

45, $R_1$ = H  $R_2$ = Me
46, $R_1$ = H  $R_2$ = $C_3H_7$
47, $R_1$ = $(CH_2)_3COOEt$  $R_2$ = Me
47a, $R_1$ = $(CH_2)_3COOEt$  $R_2$ = $C_3H_7$
48, $R_1$ = $(CH_2)_3COOEt$  $R_2$ = $C_3H_7$

44, $R_1$ = n-hexyl

Synthesis of the pyrimidines was based on orthodiaminopyrimidines as precursors. Ring closure of the orthodiamines was accomplished by treatment with thionyl chloride in the presence of pyridine. Alkylation of these 10 intermediates produced compounds 47 and 48 (disubstituted pyrimidines). A detailed description of this protocol is provided in the Examples.

E. Isoquinolone Synthesis

The isoquinolones of the inventions have the general formula (IV):

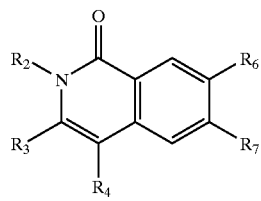

(IV)

$R_2$ is $(CH_2)_nA$ where:
A is $NH_2$, acyloxy, $SO_3H$, $PO_4H_2$, NNO(OH), $SO_2NH_2$, PO(OH)$NH_2$, $SO_2R$, or COOR where R is H, an alkyl having from 1 to 4 carbon atoms, an alkenyl having from 1 to 4 carbon atoms, tetrazolyl or benzyl;

n is any number of atoms from 1 to 7 having saturated and/or unsaturated carbon to carbon bonds, which atoms may include an oxygen or nitrogen atom in place of a carbon atom to form, respectively, ether or amino linkages;

and, preferably, $R_2$ is a ω-carboxyalkyl, ω-carboxyalkenyl, or ω-carboxyaryl having from 1 to 8 carbon atoms, wherein the aromatic group further has as a substituent A (as defined above); and $R_3$ is H, an alkyl (including aliphatic and alicyclic, and heteroalicyclic forms), alkenyl, aralkyl having 1 to 7 carbon atoms or a ω-hydroxyalkyl having from 1 to 7 carbon atoms;

$R_4$ is H, OH, $NH_2$ or O-alkyl having from 1–7 carbon atoms;

$R_5$ is H, OH, NO, $NO_2$, $NH_2$ an O-alkyl having from 1–4 carbon atoms, or X where;

X is H, any halogen, OH, SH, OR', or SR', where R is an alkyl, alkenyl, phenyl or benzyl having from 1 to 4 carbon atoms; and, $R_7$ is H, OH, NO, $NO_2$, $NH_2$ an O-alkyl having from 1–7 carbon atoms, or X where:

X is H, any halogen, OH, SH, OR', or SR', where R' is an alkyl, alkenyl, phenyl or benzyl having from 1 to 7 carbon atoms.

These compounds were synthesized by purchasing isoquinolines from Aldrich Chemical (see, FIG. 14) and adding side chains to the ring structure as described above and in the Examples with respect to the purine, pteridine and thiadiazolopyrimidine compounds of the invention. Only the 6,7-dimethoxy-1(2H)-isoquinoline compound (Aldrich # S52, 626-6) had any inhibitory effect on TNF-α production prior to addition of the side chains described above (see also, Example 7).

F. Quinazoline Synthesis

The quinazolines of the invention are synthesized according to the following scheme and are represented in structure by Compound 52:

Scheme IV (DIDEAZAPTERIDINES OR QUINAZOLINES)

Compound 52 (a quinazoline derivative; ethyl 4-(1-methyl-2, 4-dioxoquinazol-3-yl) butanoic acid) was produced as follows:

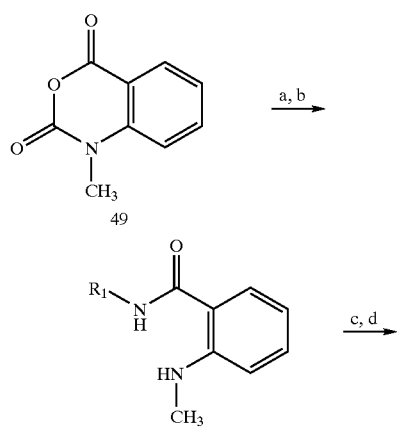

50, $R_1$ = $(CH_2)_3COOH$
51, $R_1$ = $(CH_2)_3COOEt$

-continued

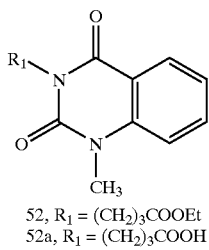

52, $R_1$ = $(CH_2)_3COOEt$
52a, $R_1$ = $(CH_2)_3COOH$

The starting material for this protocol was N-methyl isatoic anhydride. A detailed description of this protocol is provided in the examples.

G. Increasing the Water Solubility of Compounds

The carboxylic ester and acid derivatives of the compounds described above can be converted to substituted carboxylic esters, where the substituent of the ester increases the water solubility of the compounds. Particular substituents that increase the water solubility of the compounds effectively are aminoalkyl esters. The amino group of the aminoalkyl ester preferably is a secondary or tertiary amino group. The amino substituents have between 1 and 6 carbon atoms, one of which can be replaced by an oxygen atom or nitrogen atom. The preferred aminoalkyl is a tertiary amine and the amino substituents are preferably are ether groups. The most preferred aminoalkyl is N-morpholinoethyl. The carboxylic ester and carboxylic acid derivatives can be converted to the morpholinoethyl ester form by the method shown in Scheme V.

Scheme V (MORPHOLINOETHYL DERIVATIVES)

Compound 53 (an isoquinolone derivative; ethyl (6, 7-dimethoxy-1(2H)-isoquinolonyl) butanoic acid; prepared, for example, according to Example 9) converted to compound 54, a morpholinoethyl ester (isolated as a hydrochloride salt) as follows:

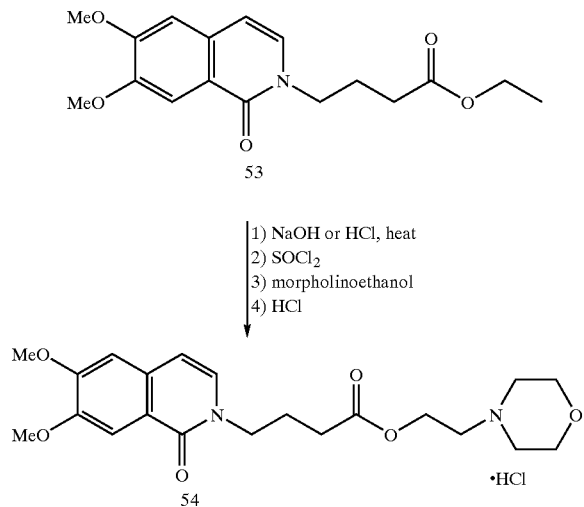

II. Methods for Use of the Inventive Compounds

The compounds of Formulas I through IV may be administered to a mammalian host to retard cellular responses associated with TNF-α and IL-1 production and activation of the ceramide-mediated signal transduction pathway. In particular, the compounds of the invention may be administered to a mammal to retard activation of ceramide-dependent intracellular biochemical pathways in target cells without inhibiting the activity of phosphodiesterase in the target cells or affecting the levels of diacylglycerol therein. As exemplified herein, the methods of the invention are expected to be of particular use in providing protection against inflammation and excessive formation of fibrotic tissue by reducing the production of TNF-α by stimulated monocytes. As further exemplified herein, the compounds of the invention (particularly the isoquinolines and pteridines) are also expected to be efficacious in providing protection against cell senescence or cell apoptosis, such as occurs as a result of trauma (e.g., radiation dermatitis) and aging (e.g., of the skin and other organs). In this context, the phrase "providing protection against" means clinically significant inhibition of cellular responses to stimuli (signals) whose transmission to the cell is facilitated in whole or in part by the ceramidemediated, sphingomyelin signal transduction pathway.

For purposes of this disclosure, therefore, inflammation, fibroblast proliferation, cell senescence and cell apoptosis in response to ceramide-mediated signal transduction through the sphingomyelin pathway will be considered to be "ceramide associated" conditions. Those of ordinary skill in the art will be familiar with, or can readily ascertain, the identity and clinical signs of specific ceramide associated conditions, and can identify clinical signs of improvement therein (such as reductions in serum levels of TNF-α and improvement in clinical health) in addition to those exemplified herein.

For administration, the compounds of the invention will preferably be formulated in a pharmaceutically acceptable carrier. Such carriers include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Exemplary of solid carriers are lactose, terra alba, sucrose, talc, gelatin, agar, pectin, acacia, magnesium stearate, stearic acid, microcrystalline cellulose, polymer hydrogels and the like. Similarly, the carrier or diluent may include any time delay material well known to the art, such as glyceryl monostearate or glyceryl distearate alone or with a wax, microcapsules, microspheres, liposomes, and hydrogels. For further reference, those of skill in the art may wish to consult the standard reference *Remington's Pharmaceutical Sciences* (which is incorporated herein by reference to illustrate knowledge in the art concerning suitable pharmaceutical carriers).

A wide variety of pharmaceutical forms can be employed. Thus, when using a solid carrier the preparation can be tableted, placed in a hard gelatin capsule in powder or pellet form, or in the form of a troche, lozenge or suppository. When using a liquid carrier the preparation can be in the form of a liquid, such as an ampule, or as an aqueous or nonaqueous liquid suspension. Topical administration via timed release skin patches is also a suitable pharmaceutical form.

Dosages of the compounds of the invention will vary depending on the age, weight and presenting condition of the host to be treated, as well as the potency of the particular compound administered. Such variables will readily be accounted for by those of ordinary skill in the clinical art. In particular, dosages will be adjusted upward or downward for each recipient based on the severity of the condition to be treated and accessibility of the target cells to the pharmaceutical formulations of the invention. Where possible, it will be preferable to administer the pharmaceutical formulations of the invention locally at the site of the target cells; e.g., into inflamed skin or by infusion to another organ of the host. Thus, dosages will also vary depending on the route of administration and the extent to which the formulations of the invention are expected to reach target cells before dilution or clearance of the formulation. Preferred routes of administration are by topical administration, local injection or parenteral infusion, although oral and intravascular routes may also be utilized.

Generally, however, based on experience with other inhibitors of intracellular responses to external stimuli (such as pentoxifylline) and the data provided herein, good results can be expected to be achieved in an adult host of about 60 kg body weight in a dosage range of about 500 to about 4,000 mg/day, preferably between about 1,000 and about 3,500 mg/day (i.e., a "therapeutically effective dosage"). These dosages may be combined with other conventional pharmaceutical therapies for inflammation and fibrosis; e.g., administration of non-steroidal anti-inflammatory medications.

The compounds of the invention vary in potency. A summary of the potency of each compound (expressed as a percentage of inhibition of intracellular responses to LPS, namely, the production of TNF-α, where responses to pure LPS=100% and are measured as the concentration of the inventive compound needed to inhibit TNF-α production by 50%) is provided in Table 1, above. Those of ordinary skill in the art will recognize that lesser or greater dosages of the compounds of the invention may be required depending on the potency of the particular compound being administered.

III. Methods for Identification of Therapeutically Effective Analogues of the Compounds of the Invention Those of ordinary skill in the art will be familiar with means to develop analogues to the compounds specifically described herein which, although not structurally identical thereto, possess the same biological activity. Such compounds are within the scope of the invention and may be identified according to the protocols described below and in the Examples.

Though exposure of cells to the compounds of the invention under controlled conditions, the responsiveness of cells to inflammatory agents and intracellular mechanisms therefor can be investigated. This information will not only better elucidate the intracellular pathways responsible for cellular responses to particular stimuli, but will also aid in the identification of anti-inflammatory and anti-fibrosis therapeutic compounds.

To identify and select therapeutic compounds for use in treating ceramide-associated conditions such as inflammation and fibrosis, cells (or intracellular components such as microsomes) which have not been exposed to an inflammatory or fibroblast proliferation inducing agent (e.g., LPS, TNF-α, IL-1, PDGF) are exposed to such an agent and the candidate therapeutic compound. Specifically, a control group of cells is incubated with a known amount of the inflammatory or fibroblast proliferation inducing agent. Treatment groups of cells are exposed to the same amount of inflammatory or fibroblast proliferation inducing agent as well as aliquots of the candidate therapeutic compound. Inflammatory responses or fibroblast proliferation in each group are detected by conventional means known to those of skill in the art (such as the assay steps described in the examples) and compared.

To identify and select therapeutic compounds for use in treating ceramide-associated conditions of cell senescence and apoptosis, cells (or intracellular components such as microsomes) which have not been exposed to a senescence or apoptosis inducing agent (e.g., cytokines such as TNF-α and exogenous stimuli such as heat, radiation and chemical agents), are exposed to such an agent and to the candidate therapeutic compound. Inhibition of senescence or apoptosis is measured as a function of cell growth. Those of ordinary skill in the art will be familiar with techniques for obtaining such measurements, examples of which are provided below.

"Therapeutically effective compounds" will be those which, when administered according to the invention and sound medical practices, provide cells with protection against ceramide-associated conditions compared to control values for cellular reactions to a ceramide-associated condition inducing agent.

The invention having been fully described, examples illustrating its practice are set forth below. These examples should not, however, be considered to limit the scope of the invention, which is defined by the appended claims.

In the examples, the abbreviation "min." refers to minutes, "hrs" and "h" refer to hours, and measurement units (such as "ml") are referred to by standard abbreviations. "mp" refers to melting point.

EXAMPLE 1

Inhibition of Cell Senescence After Serum Deprivation in Serum-Dependent Cells

Many cell types are dependent upon serum factors for growth. Thus, deprivation of such cells of serum provides a model for assessment of compounds to modulate cell responses to intracellular ceramide-mediated signal transduction. In particular, withdrawal of serum from serum-dependent cell cultures produces increased intracellular levels of endogenous ceramide and may also increase intracellular levels of endogenous diacyl glycerol (see, e.g., Jayadev, et al., *J.Biol.Chem.*, 270:2047–2052, 1995).

To evaluate the inhibitory effect of the compounds of the invention on ceramide-associated conditions in vitro, the serum withdrawal model was used. Specifically, 3T3 fibroblast cells were seeded in 96 well microtiter plates in DMEM in the presence of 10% fetal bovine serum. The cells were incubated to 90% confluence.

The medium was removed, the cells washed and reincubated in serum-free DMEM. Compound no. 37 and cell permeable ceramide were added to the wells at concentrations of, respectively, 0, 4, 40 or 400 $\mu$M compound no. 37 and 0, 5 or 10 $\mu$M of ceramide. After 24 hrs. incubation, 0.5 $\mu$Ci of [$^3$H] thymidine was added to each well for 2 hrs. DNA synthesis in the tested cell population was assessed by conventional techniques for detection of [$^3$H] thymidine incorporation. The results of this assay are indicated in FIG. 1 and establish the cell senescence inhibitory efficacy of the inventive compounds (as represented by compound no. 37).

EXAMPLE 2

Inhibition of Cell Apoptosis After CD95 Stimulation

Engagement of cell surface receptor CD95 (also known as Fas/Apo-1 antigen) triggers cell apoptosis. DX2 is a functional anti-FAS (CD95) antibody which will, on binding of CD95, activate the Smase catalysis of sphingomyelin hydrolysis and production of ceramide (see, re DX2, Cifone, et al., *J.Exp.Med*, 177:1547–1552, 1993, the disclosure of which is incorporated herein by reference for use in accessing the DX2 antibody). Thus, binding of CD95 is a model for induction of apoptosis via the sphingomyelin signal transduction pathway.

Figure 2:
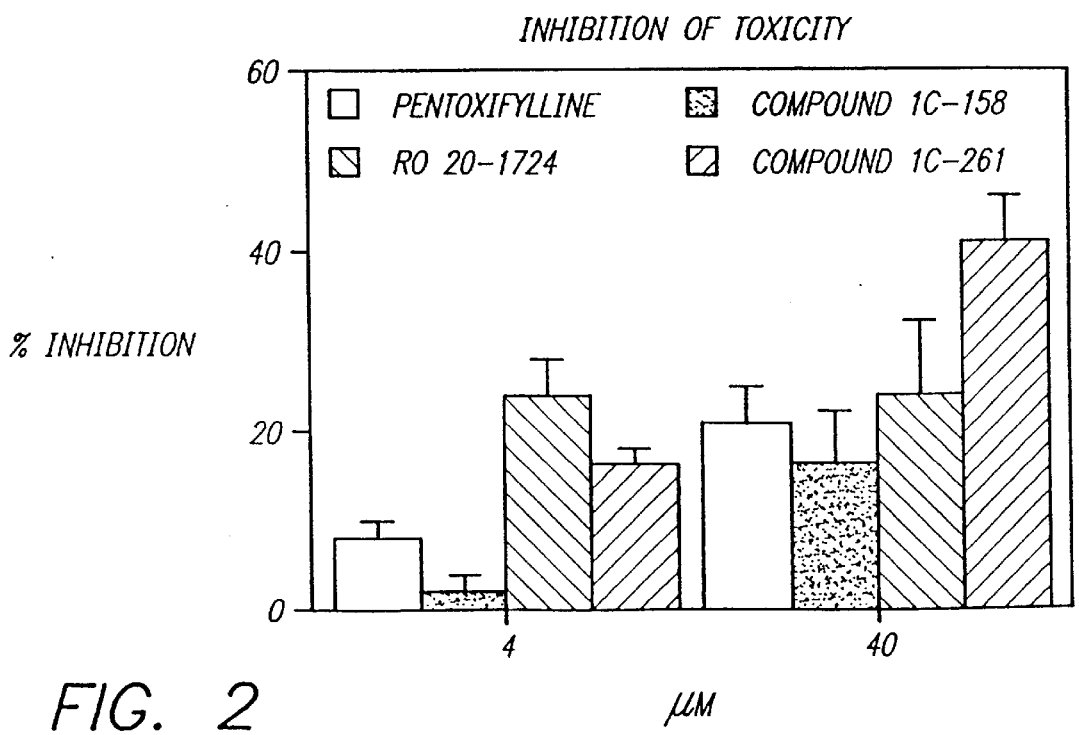
FIG. 2 is a bar graph depicting inhibition of cell apoptosis in human (Jurkat) T lymphocytes according to the invention. The inhibitory activity of two inventive compounds (nos. 37 and 6 (a purine)) was tested in comparison to like activity of pentoxyfilline and a control compound, Ro 20-1724. Activation of the sphingomyelin signal transduction pathway was stimulated by incubation of the cells with an anti-FAS monoclonal antibody (which binds CD95, a cell surface receptor which triggers cell apoptosis). Percent inhibition was measured as a function of the number of cells which excluded vital dye erythrosin B. Percent inhibition is indicated along the y axis while the concentration of compounds tested is indicated along the x axis.

To assess the inhibitory effect of the compounds of the invention on ceramide-mediated cell apoptosis, human T lymphoblasts (Jurkat) were suspended at $2 \times 10^6$ cells per ml in RPMI-1640 supplemented with insulin, transferrin, selenium and glutamine. After incubation for 2 hrs. at room temperature with either compound no. 37, compound no. 6, pentoxifylline or a control compound (Ro-1724), 25 ng/ml of anti-FAS antibody was added to each suspension. After another 2 hrs., cell apoptosis was measured as a function of the number of cells (counted by hemocytometer) that excluded the vital dye erythrosin B. The results of the experiment are indicated in FIG. 2 and establish the apoptosis inhibitory efficacy of the compounds of the invention (as represented by compounds nos. 6 and 37, particularly the latter).

To assess the inhibitory effect of the compounds of the invention on death of human lymphocytes, human peripheral blood lymphocytes were isolated from normal human blood and depleted of monocytes by adherence to a plastic substrate. Lymphocytes were then cultured in RPMI-1640 medium with 10% autologous plasma at an initial concentration of $2 \times 10^6$ cells per ml. Aliquots of the cell samples were divided and one half of the samples were incubated with either compound 37 or compound 1L-49 (an isoquinolone, the structure of which is shown in Example 7) for four days. The remaining half of the samples were allowed to rest for four days. Cell viability after four days was determined by erythrosin B dye exclusion in a hemocytometer.

Figure 13:
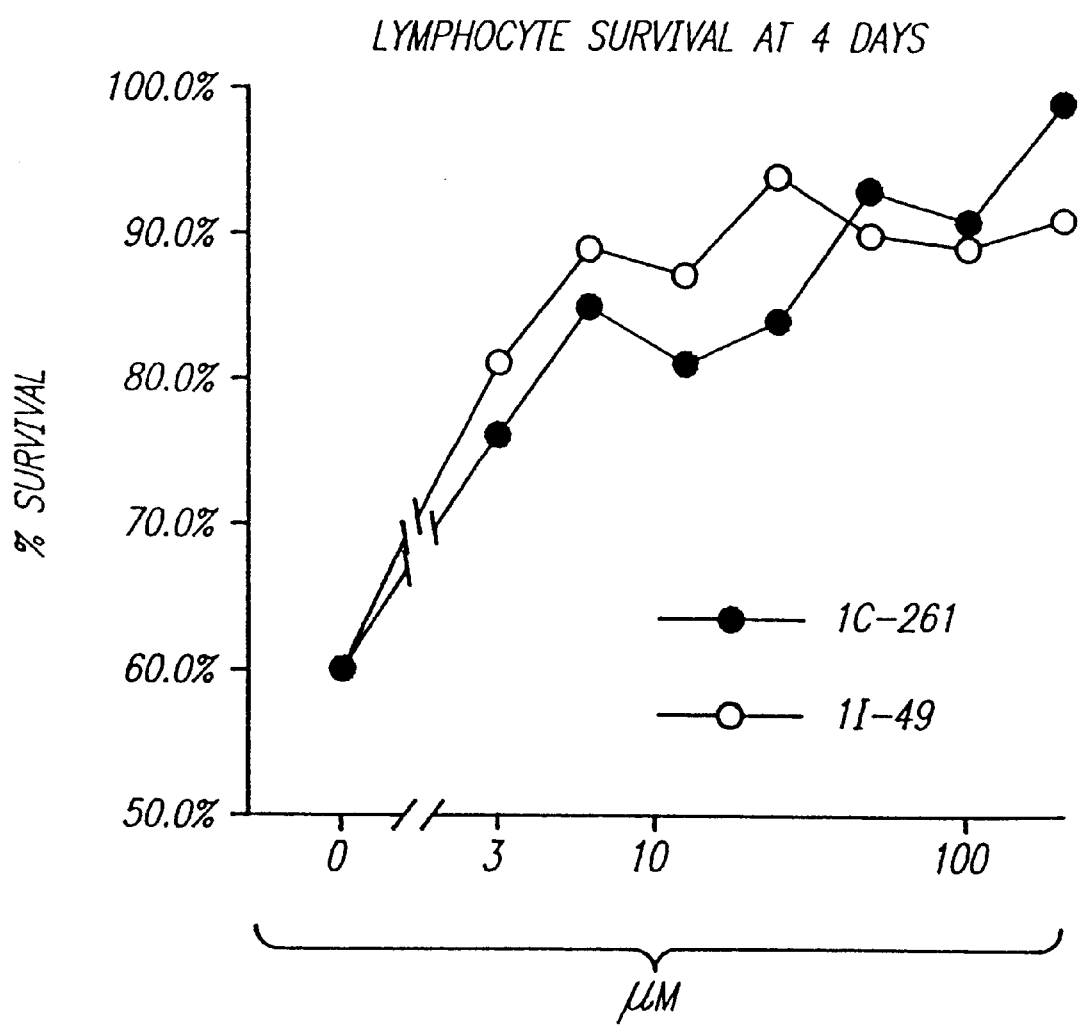
FIG. 13 depicts data indicative of the apoptopic protective characteristics of the compounds of the invention as represented by compounds 1C-261 (Compound 37) and 1I-49. Human lymphocytes were cultured in serum aliquots with the concentrations of the inventive compounds indicated along the x axis of the FIGURE. Protective effects were measured over 4 days as a function of the length of survival of the cultured cells in the presence of the inventive compounds as compared to survival of the cells in the absence of the inventive compounds. 100% survival (y axis) means that a number of treated cells all survived throughout the test period while an equal number of untreated cells died.
Figure 14A:
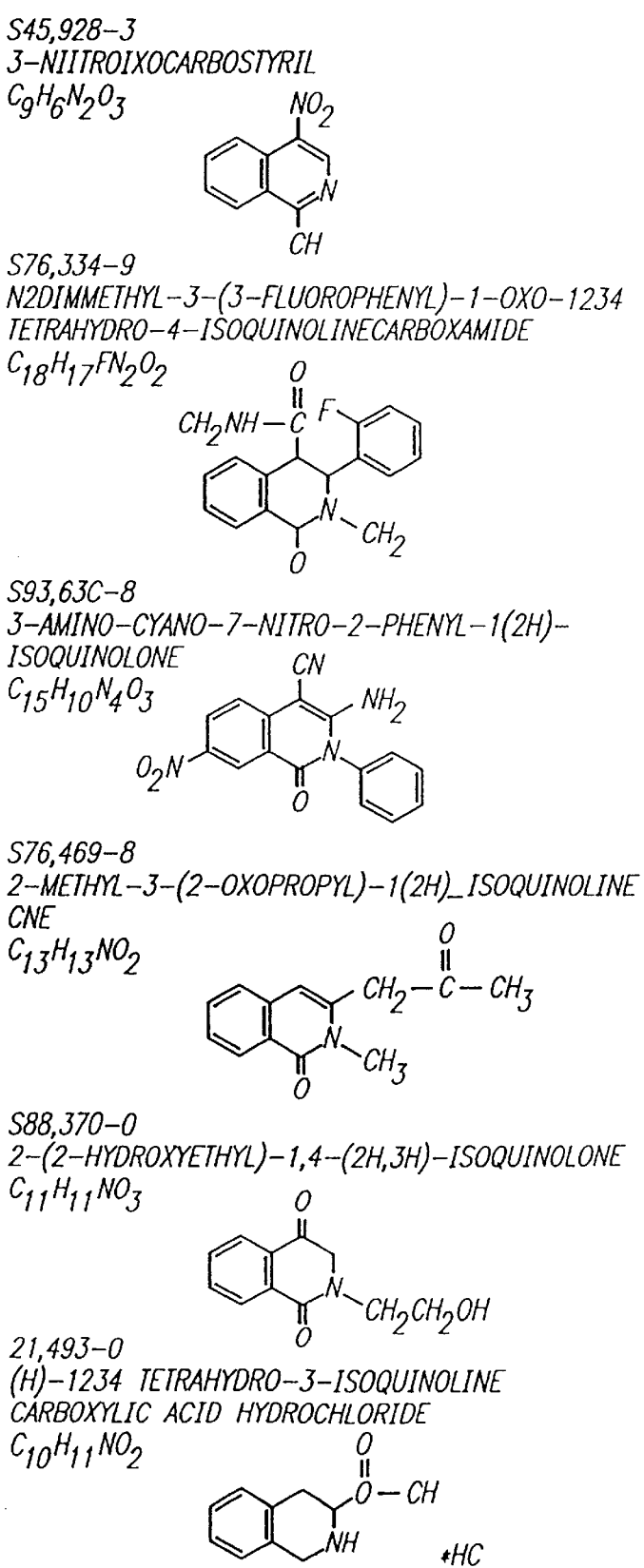
Figure 14C:
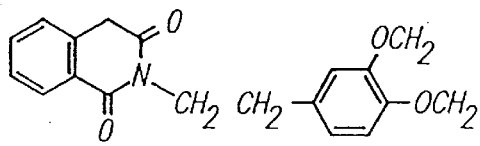
Figure 14C:
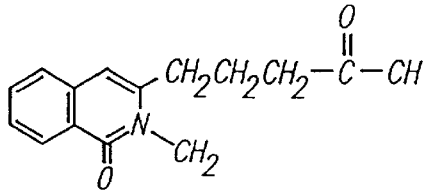
Figure 14C:
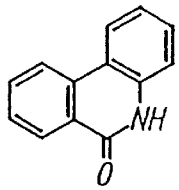
Figure 14C:
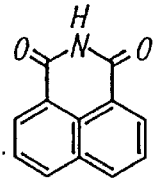
Figure 14C:
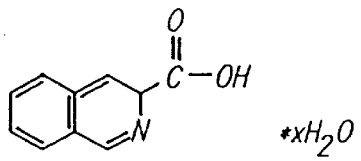

As shown in FIG. 13, at increasing concentrations, the compounds of the invention (as represented by compounds 37 and 1L-49) protected the cell sample population from death by up to 100% as compared to the survival rate of untreated lymphocytes.

EXAMPLE 3

Inhibition of the Activity of Ceramide Activated Protein Kinase

Ceramide-activated protein kinase (CaPK) is a 97 kDa protein which is exclusively membrane-bound and is believed to serve a role in the sphingomyelin signal transduction pathway. In particular, CaPK is believed to mediate phosphorylation of a peptide derived from the amino acid sequence surrounding $Thr^{669}$ of the epidermal growth factor receptor (i.e., amino acids 663–681). This site is also recognized by the mitogen-activated kinase MAP (also known as a family of extracellular signal-regulated kinases). Thus, the effect of the compounds of the invention on CaPK activity in cells is indicative of the effect that the compounds exert on signal transduction in the sphingomyelin pathway.

To that end, Jurkat cells were suspended at $2 \times 10^6$ cells per ml in RPMI-1640 medium as described in Example 2. After incubation for 2 hrs., either compound 37, 20 μM of ceramide or 25 ng/ml of anti-FAS antibody DX2 were added to each suspension and incubated for 15 mins. After centrifugation and washing, the cells were separately homogenized in a dounce homogenizer.

Figure 3:
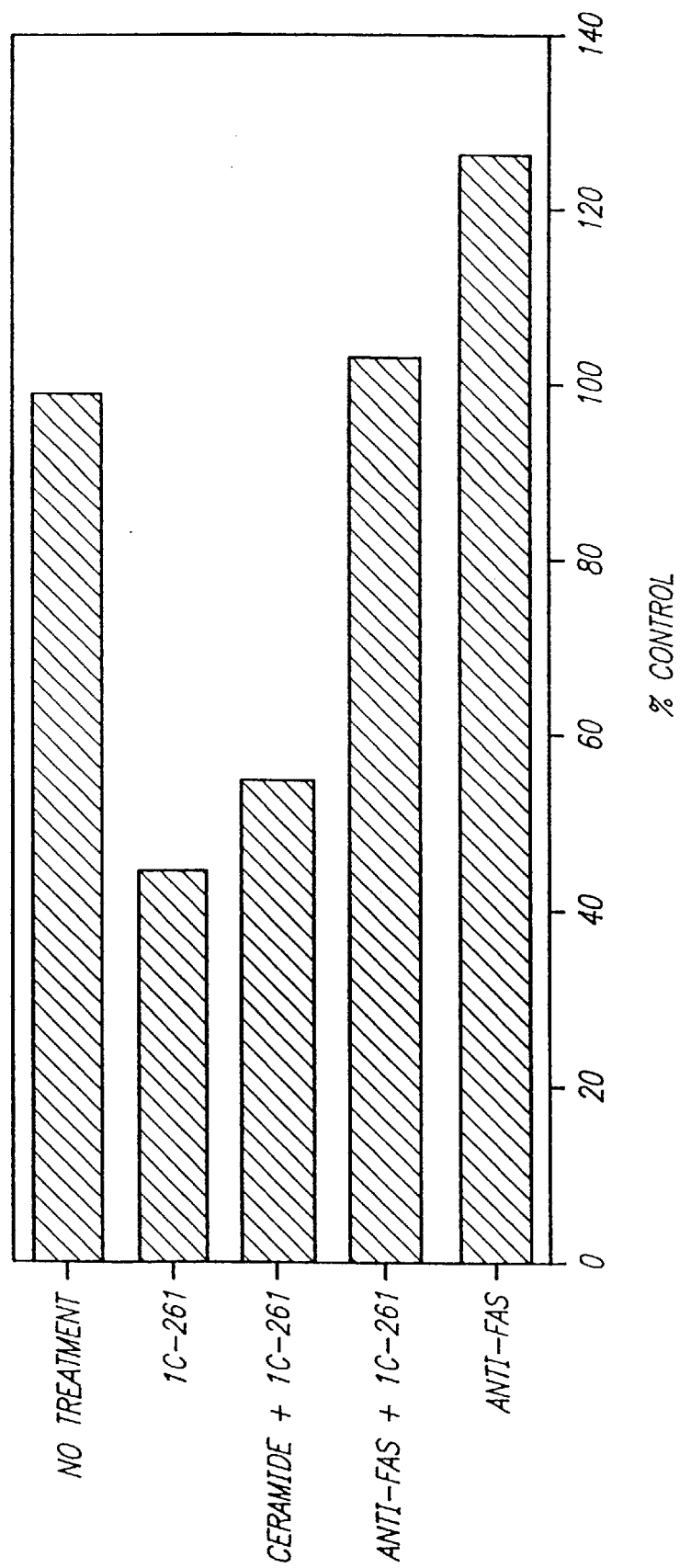
FIG. 3 is a bar graph depicting inhibition of activity on the part of CaPK in Jurkat cells according to the invention. The inhibitory activity of a compound of the invention (no. 37) was tested in the presence of either ceramide or anti-FAS. Inhibition of CaPK activity was measured as a function of phosphorylation and detected by autoradiography. The compounds the cells were incubated in are indicated along the y axis while the percent control (i.e., inhibition of CaPK) is indicated along the x axis. Shorter bars indicate greater relative inhibition.
Figure 4A:
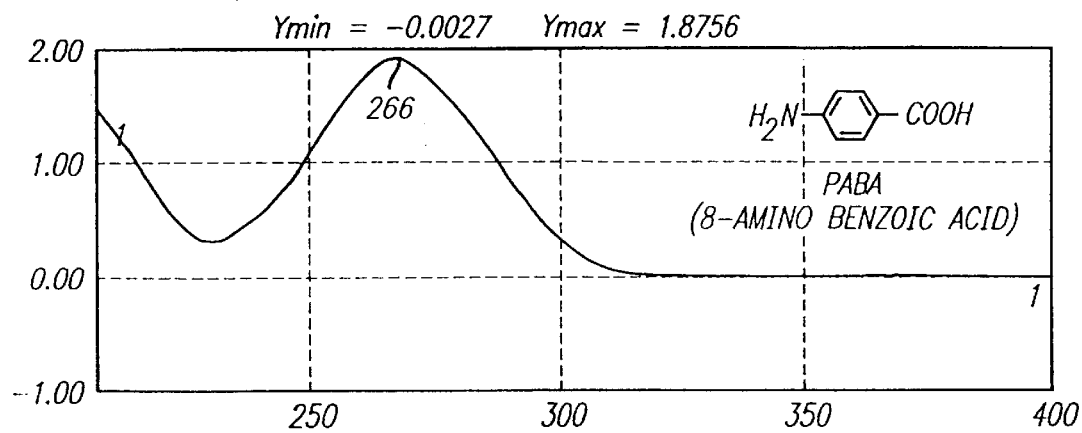
FIGS. 4(a)–(g) are copies of spectrographs indicative of absorbance of inventive compounds no. 37, no. 6, no. 37 in combination with no. 6, oxo variants of nos. 37 and 6, as well as, for comparison, PABA (p-amino benzoic acid, a common sunscreen additive) and isoquinolone. The inventive compounds absorbed through most of the UVB wavelength, while a mixture of compound nos. 37 and 6 absorbed throughout the UVB wavelength.
Figure 4B:
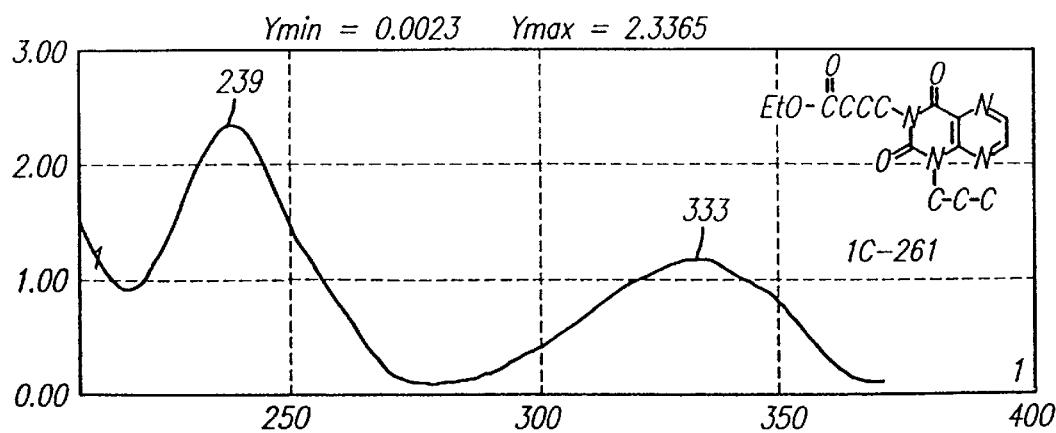
Figure 4C:
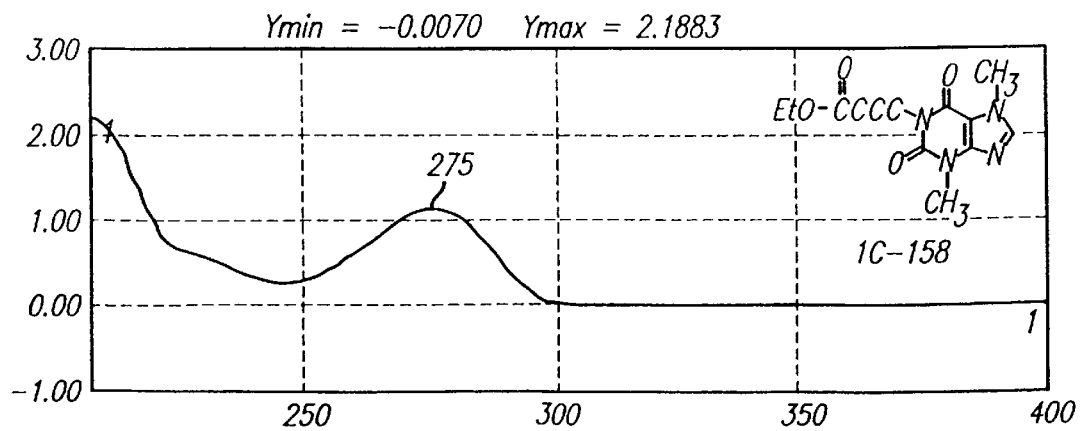
Figure 4D:
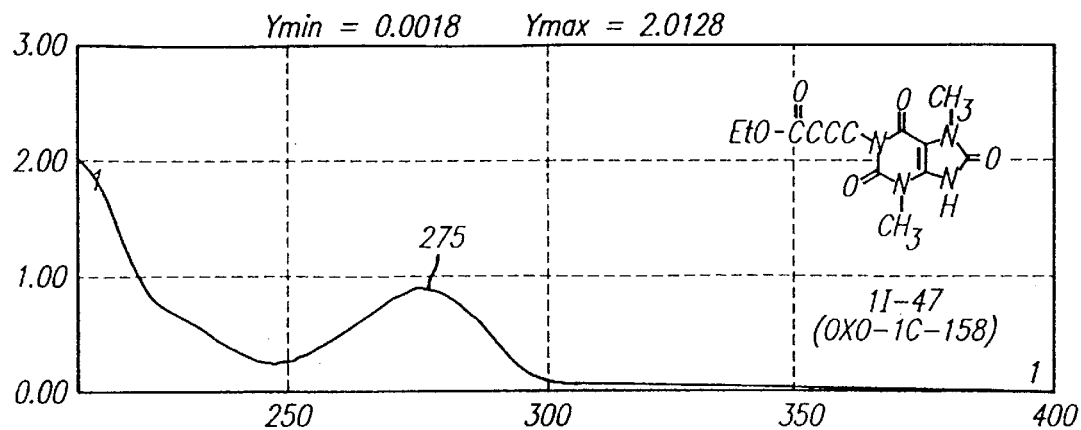
Figure 4E:
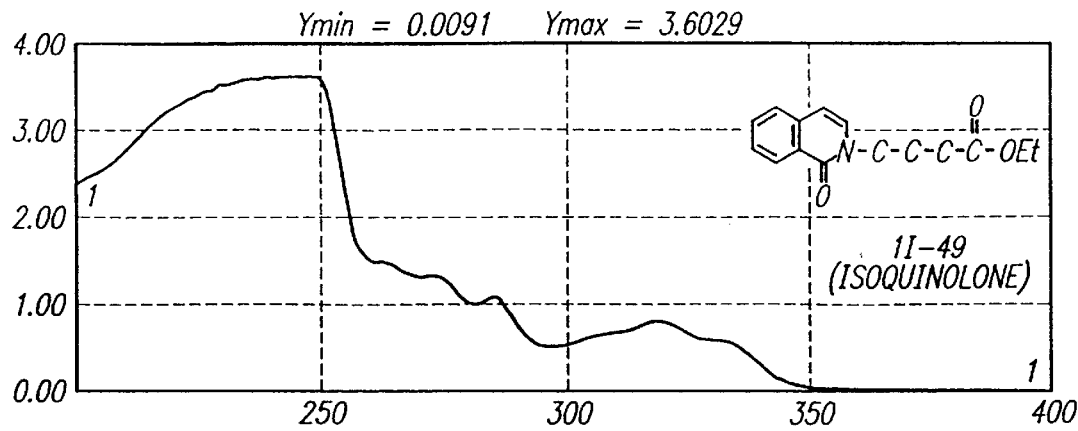
Figure 4F:
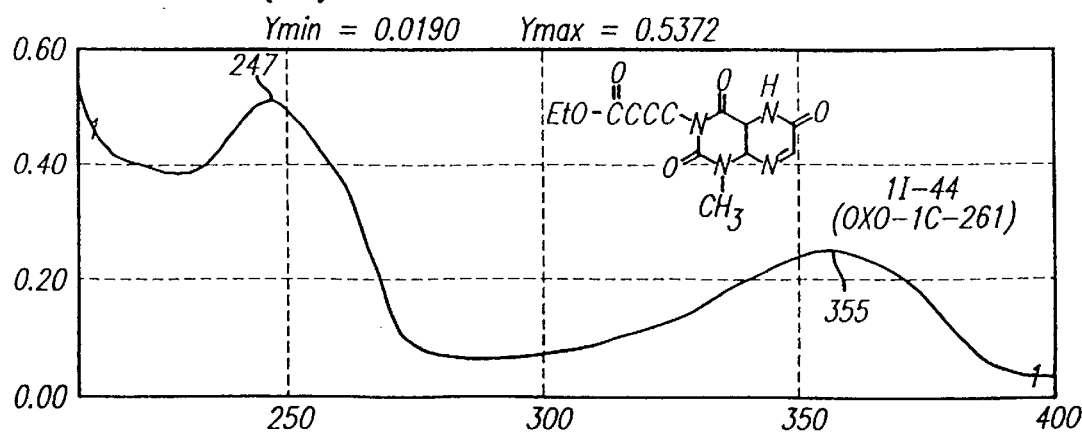
Figure 4G:
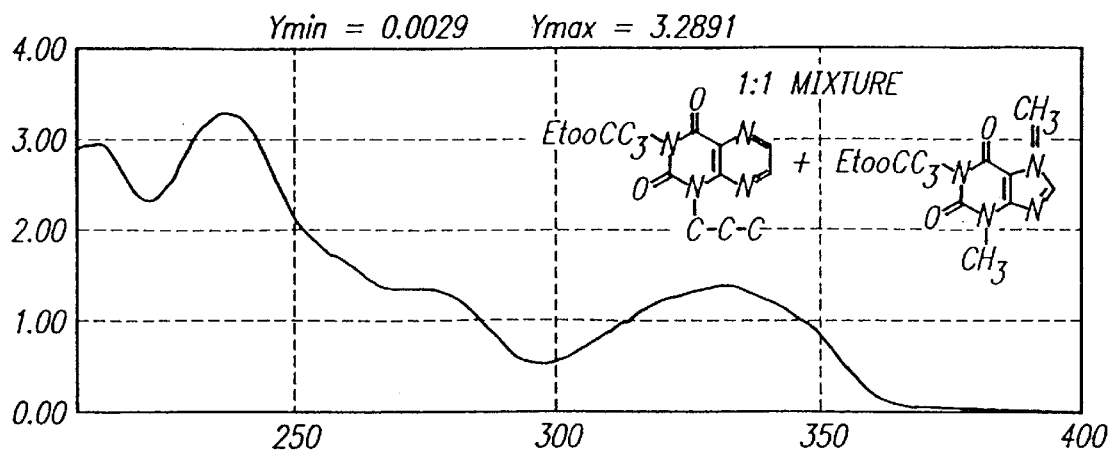

Ceramide kinase levels in each test sample were assayed as described by Liu, et al., *J.Biol.Chem.*, 269:3047–3052, 1994 (the disclosure of which is incorporated herein for reference and use in assaying ceramide kinase). Briefly, the membrane fraction was isolated from each test sample of treated cell homogenate by ultracentrifugation and run on a 10% PAGE gel. The gel was washed with guanidine-HCL, and renatured in HEPES buffer. Then [$^{32}$P]-ATP was added to the gel and left there for 10 mins. Thereafter, the gel was extensively washed with 5% TCA. Autophosphorylated kinase was detected by autoradiography. The results of this assay are indicated in FIG. 3, and establish the CaPK inhibitory efficacy of the compounds of the invention (as represented by compound 37).

EXAMPLE 4

Absorbance of UVB Radiation by the Compounds of the Invention

Radiation (particularly in the UVB wavelength) is a major cause of skin damage (including apoptosis) in humans. As indicated elsewhere above, the sphingomyelin signal transduction pathway is believed to be involved in at least the early stages of development of radiation induced dermatoses (including radiation dermatitis, sunburn and UVB induced immune suppression from radiation damage to Langerhans cells in the skin—see, e.g., Haimovitz-Friedman, et al., *J.Exp.Med.*, 180:525–535, 1994 (cellular responses to ionizing radiation); and, Kurimoto and Streilein, *J. Immunol.*, 145:3072–3078, 1992 (cutnaceous immune suppression from UVB exposure)). Thus, a compound which will inhibit cell responses to stimulus of the sphingomyelin signal transduction pathway by radiation and can be administered topically at the site of exposure would be of great benefit in retarding the damage associated with radiation exposure (e.g., through exposure to sunlight or radiation).

To assess the radiation absorbing abilities of the compounds of the invention, the ultraviolet spectra of compounds of the invention (nos. 6 and 37, alone, in combination and as 8-oxo derivatives) were evaluated and compared to those of a commercially available sunscreen additive (PABA) and isoquinoline. The spectra were identified using a KONTRON analytical instrument. As indicated in FIG. 4, the compounds of the invention (as represented by compounds nos. 6 and 37) absorbed through most of the UVB region, indicating efficacy in absorbing radiation. Surprisingly, a mixture of compound nos. 6 and 37 proved to absorb throughout the UVB region. Thus, given the somewhat greater absorbance characteristics of compound 37 vis-a-vis compound 6, it can be reasonably expected that mixtures of the two in ratios of 1:1 or greater (favoring compound 37) will have substantial synergistic efficacy in absorbing radiation and retarding its effects on cells.

EXAMPLE 5

Inhibition of TNF-α Production by the Compounds of the Invention

Figure 5B:
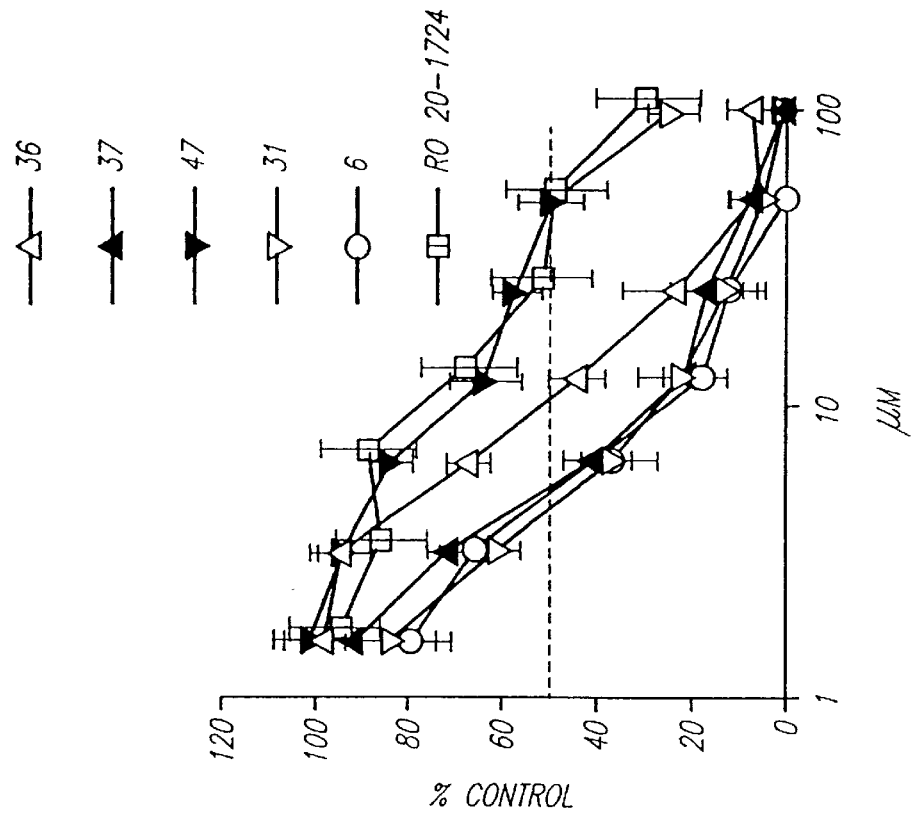
FIGS. 5(a) and (b) depict, respectively, the results of an enzyme-linked immunosorbent assay (ELISA) for TNF-α production by bacterial lipopolysaccharide (endotoxin) stimulated human monocytes incubated with the compounds of the invention and a control compound (Ro-1724, that is a known and specific inhibitor of phosphodiesterase type IV [the predominant isoform of phosphodiesterase found in monocytes and neutrophils]). Compounds tested are identified by the number assigned to them in Table 1. The horizontal axis of each graph shows the amount of each compound tested (in $\mu$M) while the vertical axis shows the IC$_{50}$ values for TNF-α production as a percentage of the production in the presence of only the control compound.
Figure 5A:
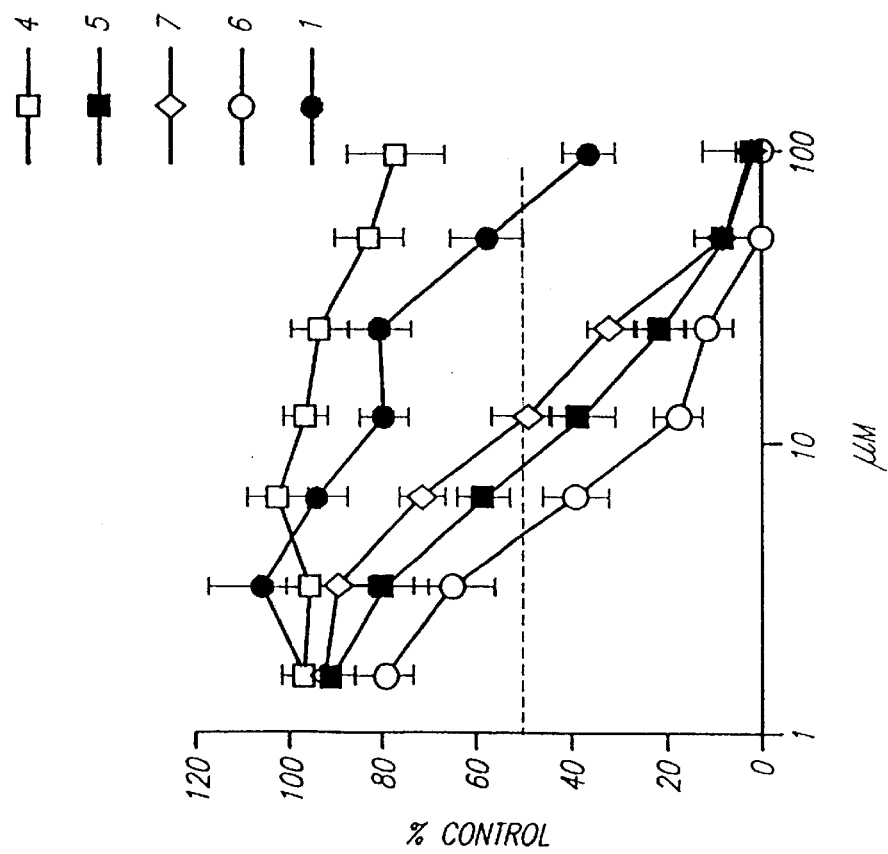

As shown in FIG. 5(a), compounds of the invention having N-1 chain lengths from 2–5 carbons are especially useful in inhibiting TNF-α production in vitro, while N-1 chain lengths of about 4 carbons (with a terminal ester) appear to be optimal in this respect (as compared to a control compound; FIG. 5(b)). Further, the esterified compounds were significantly more effective inhibitors of TNF-α production than their carboxylic counterparts. These data were obtained as follows:

Peripheral blood mononuclear cells were isolated from normal human blood on Hypaque-Ficoll density gradients. A portion of the isolated cells were further purified by adherence to gelatin coated flasks.

100 µl aliquots of monocytes were placed onto 96 well microtiter plates at a density of $5\times10^5$ cells/ml in RPMI-1640 medium containing 10% fetal bovine serum. After incubation for 24 hrs., various concentrations of the test compounds (FIG. 5) were added to the plated cells in a volume of 100 µl and incubated for 1 hr. After incubation, 1 µg/ml of LPS was added to each well.

18 hrs. after exposure of the plated cells to LPS, 100 µl of medium was collected from each well and assayed (by ELISA) for release of TNF-α, using recombinant human TNF as a standard. The sensitivity of the assay ranged from 10–100 pg/ml.

EXAMPLE 6

Figure 6:
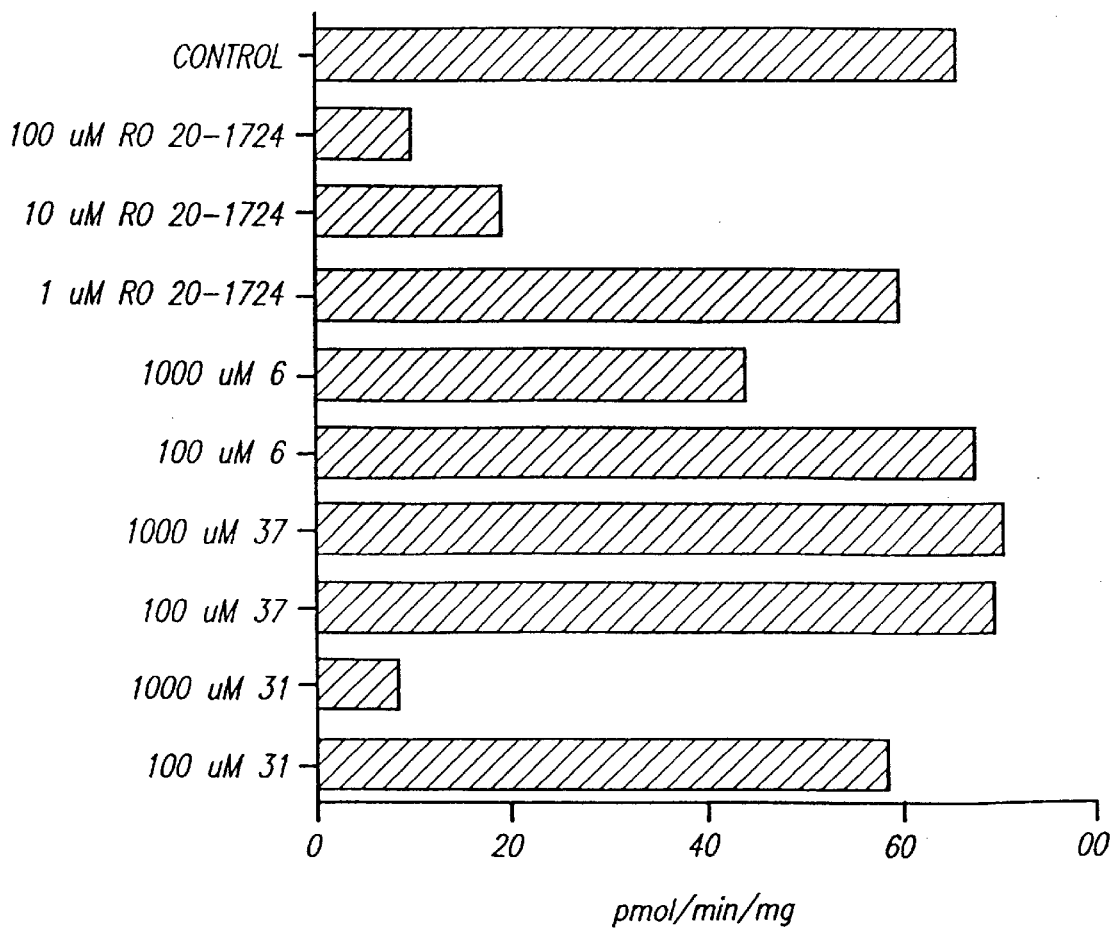
FIG. 6 is a bar graph depicting the results of an ELISA assay for inhibition of the activity of phosphodiesterase type IV by the control compound (Ro 20-1724) and several of the inventive compounds. The horizontal axis identifies the degree of inhibition achieved in pmol substrate/minutes of contact/mg of phosphodiesterase type IV. The amounts of each compound tested are identified along the vertical axis. Compounds tested are identified by the number assigned to them in Table 1.

Relatively Low Inhibition of Phosphodiesterase IV Activity by Compounds of the Invention As shown in FIG. 6, there appears to be little correlation between the efficacy of the compounds of the invention in inhibiting the activity of phosphodiesterase and inhibiting activity of TNF-α. For example, the most active pteridine compound in inhibiting TNF-α production in vitro (#37) was a very poor inhibitor of phosphodiesterase IV, even at micromolar concentrations.

These data confirm that the compounds of the invention do not target phosphodiesterase to control TNF-α production. The data were obtained as follows:

The reaction was started with the addition of PDE and incubated at 37° C. for 10 minutes, then terminated by boiling for 2 minutes. 500 µl of 0.1 M HEPES/0.1 M NaCl (pH 8.5) was added to each tube, then the reaction mixture was applied to a boronate column. Unreacted CaMP was washed off with Hepes/NaCl and the reaction mixture eluted with acetic acid. Recovery was determined with the $[^{14}C]$-AMP.

EXAMPLE 7

Figure 7:
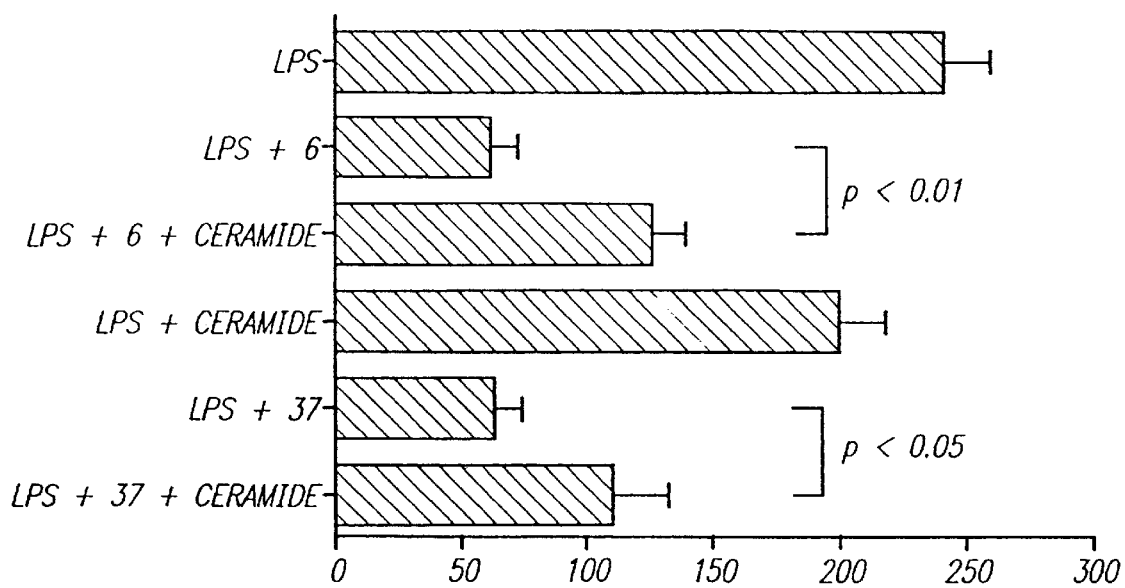
FIG. 7 is a graph depicting the results of an assay for in vivo leukopenia in mouse blood in response to lipopolysaccharide (LPS). Leukopenia induced by LPS is mediated by TNF. Hence, this model assesses both TNF production and action. Compounds tested for inhibition of leukopenia are identified by the number assigned to them in Table 1. Along the x axis of the graph, the numbers correspond to the number of white blood cells detected as cells/ml of fluid. The results (shown by bars) are expressed in terms of a percentage of the leukopenia response (based on neutrophil content) to pure LPS, in absence of other compounds.
Figure 8:
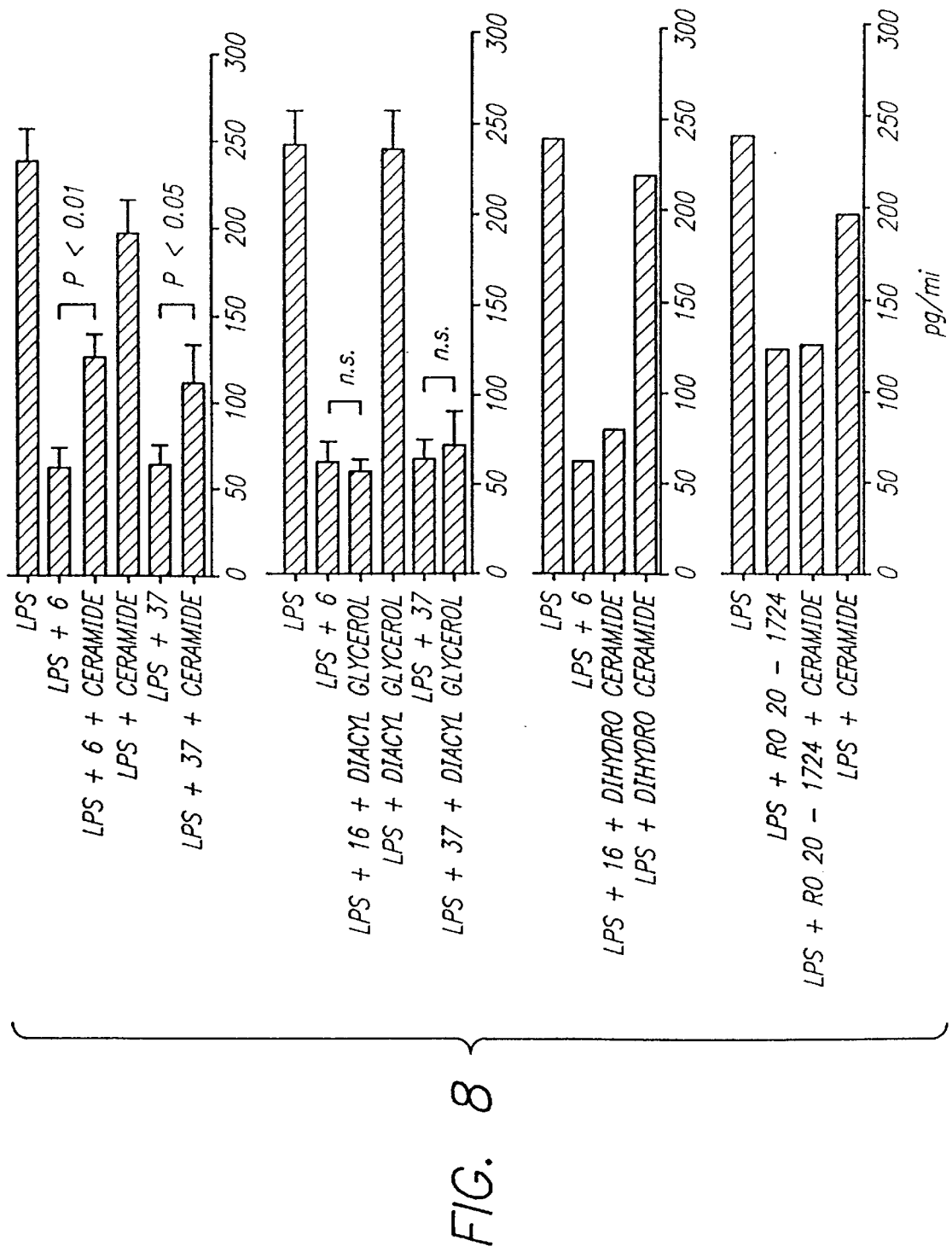
FIG. 8 depicts the results of an assay for inhibition by compounds of the invention (nos. 37 and 6) of the effects of a cell permeable ceramide analog (C$_2$-ceramide), dihydro ceramide and diacyl glycerol on TNF-α production by human monocytes. Inhibition of TNF-α production was measured by ELISA; the results are indicated in pg/ml of TNF-α along the x axis.
Figure 9:
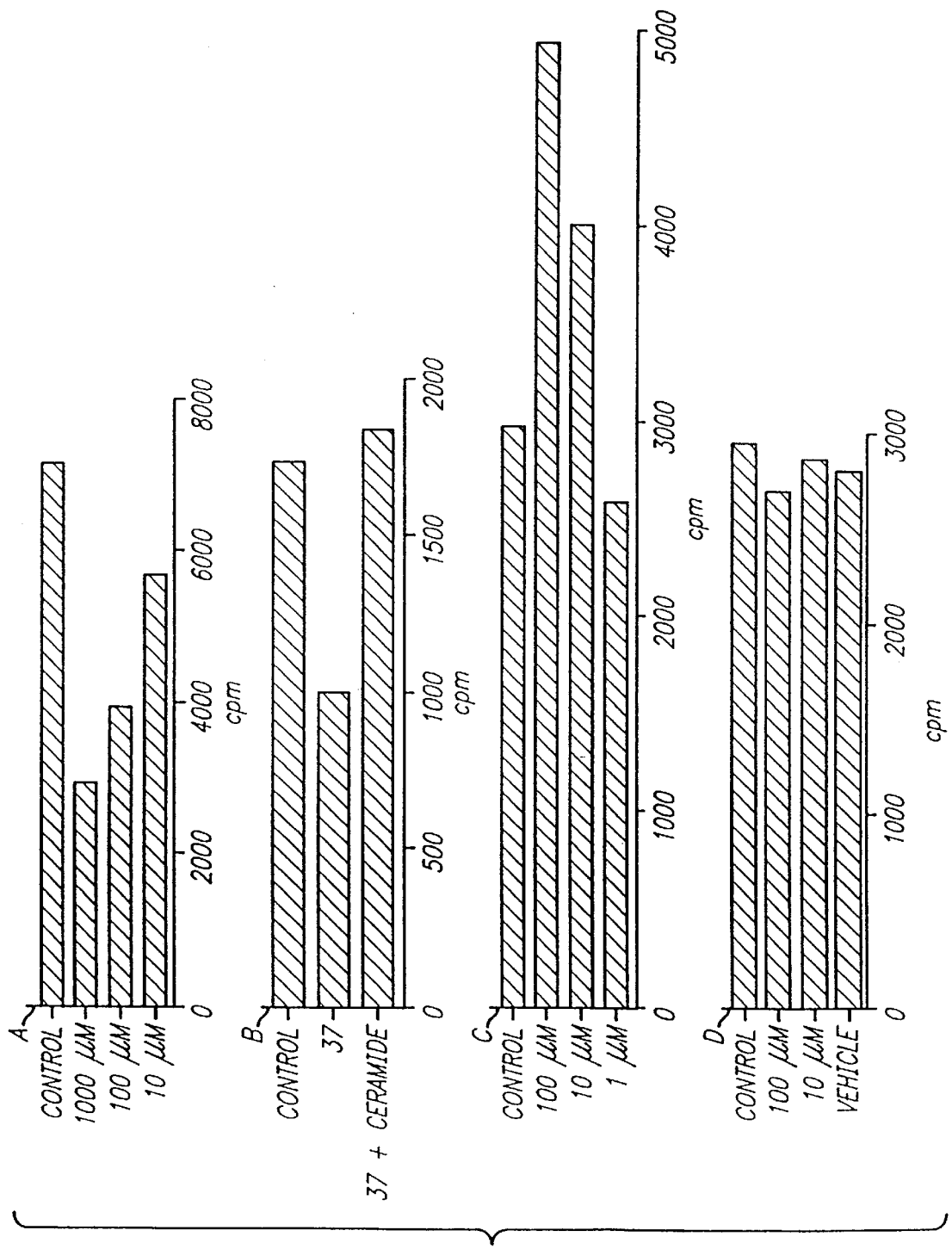
FIG. 9 depicts the results of an assay for inhibition by a compound of the invention (no. 37) to prevent the stimulatory effects of C$_2$—ceramide or protein kinase C activity in human lymphocyte extracts. Inhibitory effects were assessed as a measure of DNA synthesis; [³H] thymidine incorporation detection is indicated along the y axis.

In vivo and in vitro Leukopenia in Response to LPS and Inhibition of Same by the Compounds of the Invention As shown in FIGS. 7 through 9 and Table 1, the compounds of the invention effectively reduce cellular response to LPS, a known inducer of TNF-α production. In the presence of ceramide, the inhibitory activity of the compounds of the invention on LPS induced leukopenia (a phenomenon dependent on TNF-α induced surface expression of the P-selection class of adhesion molecules) was enhanced (FIG. 7). However, the inhibitory activity of the compounds of the invention was essentially unaffected by diacylglycerol (FIG. 8), indicating that the mode of action of the compounds of the invention are not dependent on hydrolysis of phosphatidic acid. These data were obtained as follows:

The leukopenia inhibitory capacity of the test compounds was determined by intraperitoneal administration of 0.5 µg of LPS in saline to ICR female mice (age 6–8 weeks; weight 19–23 g). One hour before receiving the LPS, the mice received the test compound by intraperitoneal injection at a dose of 50 mg/kg (in isotonic saline). Two hours after injection of LPS, 200 µl of blood was collected from each mouse into a heparinized tube and the total count of nucleated cells determined in a hemocytometer (FIGS. 7 and 9).

Calcium independent protein kinase activity was measured, using a 1% triton X-100 extract of Jurkat cells ($5\times10^8$/ml). The reaction mixture consisted of 20 mM Tris HCl pH 7.5, 20 mM $MgCl_2$, 20 µM ATP containing 200,000 cpm [γ32P] ATP, and 50 µM Myelin Basic Protein. The extract was pre-incubated with A) compound 37 B) compound 37 with or without 10 µM ceramide C) ceramide or D) dihydro ceramide for 15 minutes, followed by addition of substrate and ATP, and incubation at 30° C. for 5 minutes. The total count of nucleated cells was measured in a hemocytometer (FIG. 9). The same protocol was followed to obtain the results shown in FIG. 8 (with the addition of diacyl glycerol to some of the test mixtures).

Figure 10:
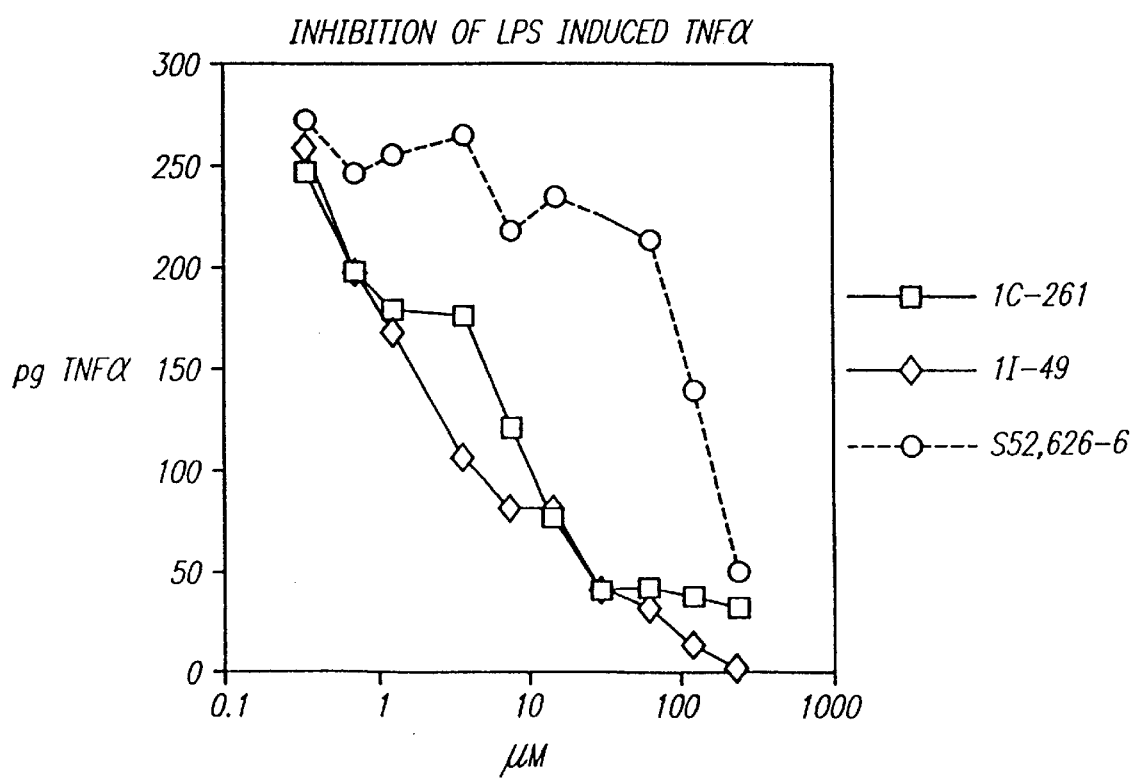
FIG. 10 depicts the results of an assay for in vitro TNF-α production by human macrophages in response to lipopolysaccharide (LPS) and inhibition of that production by pteridine and isoquinolone compounds of the invention (nos. 37 and 11–49). Along the x axis of the graph, the numbers correspond to the concentration of TNF-α detected in pg/ml.

An isoquinoline compound of the invention was also tested in vitro for its inhibitory efficacy with respect to LPS induced TNF-α production in human cells. The structure of the compound, 1I-49, is described below:

Human macrophages were cultured in 96 well microtiter plates and incubated with LPS. µAliquots of the stimulated cells were then incubated with, respectively, 0.1, 1, 10, 100 or 1000 µM of 1I-49, compound 37 and a commercially available isoquinoline (6,7-dimethoxy-1(2H)-isoquinoline from µAldrich Chemical; labelled S52-626-6 in FIG. 10) which, like the compounds of the invention, has an oxygen ortho to a ring nitrogen but, unlike the compounds of the invention, lacks a side chain substituent as described above (1L-49 is representative of the isoquinolone compounds of the invention having the side chain substituents described elsewhere above). The inhibitory efficacy of each compound was measured as a function of TNF-α reduction in µg/ml. The results of the experiment are indicated in FIG. 10 and establish that the compounds of the invention (represented by 1I-49 and compound 37) have inhibitory efficacy with respect to reduction in LPS induced TNF-α production by human cells. Other isoquinolines tested (FIG. 14) did not exert inhibitory activity in the absence of the side chain substituents added according to the invention.

EXAMPLE 8

Figure 11:
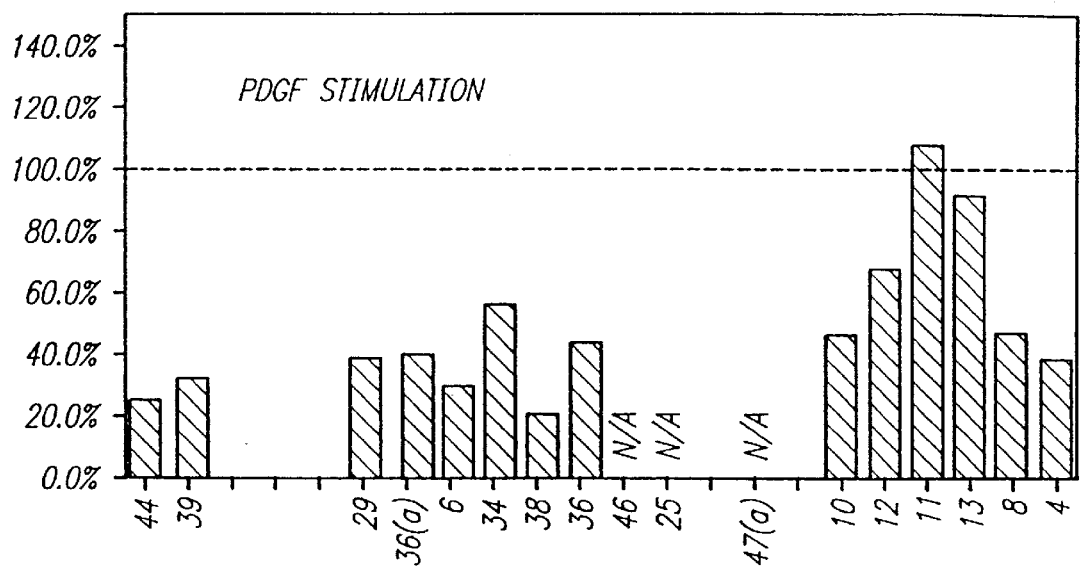
FIG. 11 depicts inhibition of PDGF induced fibroblast proliferation among 3T3 fibroblasts in response to the inventive compounds. The compounds tested are identified along the x axis by the numbers assigned to them in Table 1. Inhibitory effects were assessed as a measure of DNA synthesis; [³H] thymidine incorporation detection is indicated along the y axis.
Figure 12:
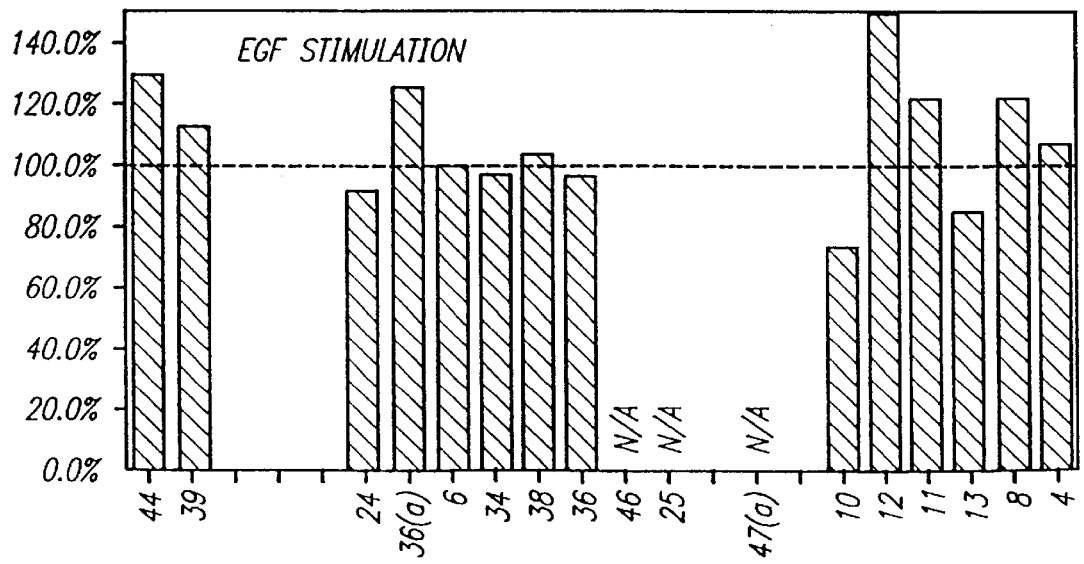
FIG. 12 depicts inhibition of EGF induced fibroblast proliferation among 3T3 fibroblasts in response to the inventive compounds. The compounds tested are identified along the x axis by the numbers assigned to them in Table 1. Inhibitory effects were assessed as a measure of DNA synthesis; [³H] thymidine incorporation detection is indicated along the y axis.

Fibroblast Proliferation in Response to LPS and Inhibition of Same by the Compounds of the Invention As shown in FIG. 11, PDGF induced fibroblast proliferation was selectively inhibited by the compounds of the invention. In addition, the compounds were shown not to be cytostatic or cytotoxic, insofar as they did not alter EGF-triggered mitogenesis in the cells tested (FIG. 12).

These data were obtained as follows:

Mouse fibroblast line 3T3 cells (American Type Culture Collection #CCL 92) were seeded into 96 well plates in complete medium and allowed to grow to confluence. The medium was then replaced with medium-free serum and the cells incubated for 24 hrs.

The test compounds were then incubated with the cells for 1 hr before addition of 5 ng/ml human PDGF or EGF was added to each well. After another 24 hrs, 1 µCi of $[^3H]$-thymidine was added to each well. 4 hrs later the cells were harvested onto glass fiber filters and the cellular incorporation of $[^3H]$-thymidine was measured by liquid scintillation counting (FIGS. 11 and 12).

EXAMPLE 9

Synthesis of Compounds 2, 4–8 and 10–13

General µAlkylation Procedure for Compounds 4–8, 10, 11 (Method A):

Theobromine or 8-bromotheobromine (2 mmol) was combined with anhydrous $K_2CO_3$ (2.5 mmol) and dry DMF (15 mL) and the mixture was brought to 75° C. The appropriate alkyl halide (2.5 mmol) was added and the mixture was stirred at 75° C. for 2–18 h. The reaction mixture was cooled, poured into water (125 mL) and extracted with ethyl acetate (2×75 mL). The organic layer was dried over magnesium sulfate and evaporated to yield a colorless oil or white solid which was triturated with ethyl ether. The resulting solid, often analytically pure, may be purified further if desired by crystallization from a small amount of ethanol. Yields 58–89%. Compounds 15–17, 31, 36–38, 41, 43, 47, and 48 (described below) were prepared by this same procedure only using the appropriate precursors in place of theobromine.

General Thiation Procedure for Compounds 12 and 13:

The 8-bromoxanthine 10 or 11 (0.25 mmol) was suspended in anhydrous ethanol (10 mL) and heated to reflux. NaSH.$(H_2O)_x$ (2.5 mmol) was added and the mixture became clear, green almost immediately. The mixture was stirred under reflux for 30 min, cooled and evaporated onto silica gel. Flash column chromatography using 5–7% MeOH in $CH_2Cl_2$ provided a 63% and 75% yield of 12 and 13, respectively as white solids. Note: Compound 13 was found by $^1$H NMR to be the ethyl ester due to transesterification under the reaction conditions.

$^1$H NMR spectra and elemental analyses or exact mass data were consistent with the assigned structures (see, Table 2 following Example 9).

EXAMPLE 10

Synthesis of Compounds 24, 25, 31 and Intermediates

General Procedure for C-Nitrosation of Pyrimidines (Compounds 18–20, 27, and 32):

The pyrimidine (15 mmol) was suspended in N HCl (30 mL) and an aqueous solution of sodium nitrite (20 mmol in 10 mL) was dripped in with stirring over 10 min. The suspension went from off-white to purple almost immediately. Stirring was continued for 1 h, pH adjusted to 5 with ammonia water and the purple solid product collected to provide 75–90% yield after drying. The characteristic lack of the C-5 proton in the $^1$H NMR was evident for each compound (Table 2).

General Procedure for the Reduction of 5-Nitroso to 5-Amino Pyrimidines (Compounds 21–23, 28, and 33):

The 5-nitrosopyrimidine (15 mmol) was suspended in water (50 mL) and heated to 80–90° C. With stirring, sodium hydrosulfite (45 mmol) was added in portions over 5 min. The color quickly changed from purple to light green and stirring was continued an additional 10 min. The mixture was cooled in ice and filtered. The filtered solid was washed with cold water, EtOH and $Et_2O$ to provide the orthodiamine in 70–88% yield as a tan to pale green solid.

Synthesis of 1-n-Hexyl-3-methyluric Acid Intermediate (24)

The nitrosopyrimidine 19 (270 mg, 1.06 mmol) was dissolved in ethanol (20 mL) with warming and palladium on carbon (75 mg, 10%) was added under argon. Hydrogenation was performed at room temperature and 15 psi for 2 h, filtered to remove catalyst and evaporated to dryness. The residue was combined with urea (600 mg, 10 mmol) and heated neat on the hot plate with stirring. The temperature reached 140° C. which produced a clear melt and was maintained for about 10 min. with additional urea added (1 g). Upon cooling the melt solidified and was dissolved in n NaOH (25 mL) and boiled with decolorizing carbon for 10 min., filtered and acidified to pH 3–4 while hot. The resulting precipitate was collected after cooling and washed with water and dried to yield 160 mg (57%) of 24 as an off-white solid with the following characteristics: mp>290° C. dec. $^1$H NMR (500 MHZ, DMSO-$d_6$) δ11.80 and 10.73 (2s, 2H, N-7 H. N-9 H), 3.78 (t, 2H, N-$CH_2$), 3.30 (s, 3H, N—$CH_3$, under $H_2O$ signal), 1.48 (m, 2H, 2'$CH_2$), 1.24 (m, 6H, 3', 4', 5' $CH_2$), 0.85 (t, 3H, $CH_3$). Analysis: $C_{12}H_{18}N_4O_3$ (C, H, N; Table 2).

Synthesis of 3-Methyl-8-thiouric Acid (25) Intermediate

The pyrimidinediamine 33 (100 mg, 0.63 mmol) was combined with potassium ethyl xanthate (810 mg, 5 mmol) and DMF (10 mL) and heated at 100° C. The suspension became green almost immediately and reaction was complete after 30 min. by TLC. After a total reaction time of 1 h, the mixture was cooled, filtered and washed with $Et_2O$, dried to yield an off-white solid (310 mg) which presumably contained the unreacted potassium ethyl xanthate and the potassium salt of the desired product. The solid was suspended in water (5 mL) and heated to dissolve. Glacial acetic acid was added to pH 5 and a vigorous effervescence was noted. A white solid formed which was filtered warm and washed with water, then ethanol and dried to yield 99 mg (79%) of the title compound. $^1$H NMR (DMSO-$d_6$) δ13.40, 12.92 and 11.80 (3br s, 3H, NHs), 3.28 (s, 3H, $CH_3$). Analysis: $C_6H_6N_4O_2S$ (C, H, N; Table 2).

Synthesis of 3-n-Propylxanthine (29) Intermediate

The pyrimidinediamine 28 (750 mg) was combined with diethoxymethyl acetate (7 mL) and heated at 80° C. for 2 h. The mixture was evaporated to dryness and water (5 mL) was added and the mixture heated for 20 min. to near boiling. The resulting solution was then allowed to evaporate slowly to yield off-white crystals. Yield 680 mg (86%); mp 282–284° C., Lit.[15] 291–292° C.

EXAMPLE 11

Syntheses of Compounds 36–39, 41 and 43 and Intermediates

General Procedure for Ring Closure of Pyrimidinediamines to Pteridines:

The orthodiamine 28 or 33 (2 mmol) was suspended in water (20 mL) and heated to above 70° C. before a solution of glyoxal-sodium bisulfite addition product (10 mmol in 25 mL water) was added with stirring. The pale green suspension slowly became light amber and clear. After heating 5 min TLC indicated reaction was complete. The mixture was cooled and extracted with ethyl acetate (5×40 mL), dried over $MgSO_4$ and evaporated to yield the 1-methyl (34) or 1-n-propylpteridine (35) in 71 and 78%, respectively. $^1$H NMR showed the appearance of two aromatic signals at about 8.74 and 8.55 as doublets (J=2.5 Hz) for both compounds.

Synthesis of 6,7-Diethyl-1-methylpteridine-2,4-dione (40) Intermediate

Compound 33 (200 mg, 1.27 mmol) was suspended in acetonitrile (5 mL) and 3,4-hexanedione (185 gL, 1.52 mmol) was added. The mixture was heated at 70° C. for 15 min with minimal product formation due to insolubility of 33. Therefore DMF (3 mL) and water (3 mL) were added and the temperature was raised to 100° C. After 90 min total reaction time the mixture was cooled and poured into water (100 mL) and extracted with ethyl acetate (3×75 mL). The organic layer was dried over $MgSO_4$ and evaporated to provide the colorless crystalline product. Yield 240 mg (81%); mp 218–222° C.; $^1$H NMR (DMSO-$d_6$) δ11.78 (br s, lH, NH), 3.46 (s, 3H, $NCH_3$), 2.95 and 2.93 (2q, 4H, $2CH_2$ of ethyls), 1.28 and 1.23 (2t, 6H, $2CH_3$ of ethyls). Analysis: $C_{11}H_{14}N_4O_2$ (C, H, N; Table 2).

Synthesis of 1-Methyl-6-phenylpteridine-2,4-dione (42) Intermediate

The nitrosopyrimidine 32 (220 mg, 1.28 mmol) was mixed thoroughly with phenethyl amine hydrochloride (1.5 g, 9.5 mmol) and heated in an open beaker on the hot plate. After a few minutes at about 160° C. the purple reaction mixture fused to a brown paste. TLC indicated many products so sulfolane (1 mL) was added and heat was continued for 15 min. The reaction mixture was heated in water (10 mL) and then diluted 50 mL in water and extracted with ethyl acetate (2×50 mL), the organic layer dried over $MgSO_4$ and then concentrated. The residue was flash chromatographed on silica gel using 4% MeOH in $CH_2Cl_2$. Yield 75 mg (23%) of 42 as a pale yellow-orange solid. mp>307° C. dec.; $^1$H NMR (500 MHZ, DMSO-d6) δ11.95 (br s, 1H, NH), 9.37 (s, 1H, C-7 H), 8.17 (m, 2H, 2', 6' phenyl), 7.55 (m, 3H, 3', 4', 5' phenyl), 3.51 (s, 3H, $NCH_3$). Anal. $C_{13}H_{10}N_4O_2$ (C, H, N).

EXAMPLE 12

Synthesis of Compounds 44, 47 and 48

General Method for Ring Closure of Pyrimidines to Thiadiazolo-pyrimidines (Compounds 44–46):

The orthodiamine 23, 27, or 32 (2.3 mmol) was suspended in dry acetonitrile (5 mL) and dry pyridine (1.5 mL) was added. Thionyl chloride (1 mL, 13.7 mmol) was added quickly and the mixture, which became clear and darkened, was heated at 60° C. for 10 min. The mixture was then cooled and poured into n HCl (40 mL) with stirring. The resulting yellow solution was extracted with ethyl acetate (3×40 mL), dried over $MgSO_4$ and evaporated to yield a pale yellow solid which was triturated with ether. Yield 65–74%.

Alkylation of these intermediates yielded the disubstituted products 47 and 48.

EXAMPLE 13

Synthesis of Compounds 50 and 52

Ethyl 4-[(2-methylamino)benzoyl]aminobutanoate (51)

A mixture of N-methylisatoic anhydride (3.5 g, 19.8 mmol) was combined with 4-aminobutyric acid (2.5 g, 24.3 mmol) in dry DMF (50 mL) and heated at 100° C. for 2 h. TLC indicated reaction to be complete and the DMF was removed in vacuo. The residue was used directly for esterification which was accomplished by dissolving the residue in 100% ethanol (50 mL) and adding chlorotrimethyl silane (2.5 mL, 20 mmol). The mixture was heated at 65° C. for 6 h and then evaporated to yield a brown syrup. Crude yield 87% from isatoic anhydride. A small sample was purified for characterization and biological testing by preparative TLC using 7% MeOH in $CH_2Cl_2$. The remainder of the material was used directly for preparation of compound 52. Analysis: $C_{14}H_{20}N_2O_3$ (C, H, N; Table 2).

Ethyl 1-Methyl-1,4-dihydro-2,4-dioxo-3(2H)-quinazolinebutanoate (52):

The residue from 51 was combined with ethyl chloroformate (10 mL) and heated at 90° C. for 1 h. The mixture was cooled and poured into saturated aqueous sodium bicarbonate (50 mL) with stirring and after 10 min extracted with ethyl acetate (2×75 mL). The organic layer was dried over $MgSO_4$ and evaporated to yield a brown syrup. The crude product was flash chromatographed on silica using 3% MeOH in $CH_2Cl_{12}$ to yield g (%) of 52 as a thick oil. $^1$H NMR (500 MHZ, DMSO-d6) δ7.27–7.42 (2m, 4H, C-5,6,7,8), 4.04 (t, 2H, $CH_2$ of ethyl), 3.88 (m, 2H, $NCH_2$), 3.11 (s, 3H, $NCH_3$), 2.33 (t, 2H, $2'CH_2$), 1.71 (m, 2H, $3'CH_2$). Analysis: $C_{15}H_{18}N_2O_4$ (C, H, N; Table 2).

TABLE 2

ANALYSIS OF SELECTED INVENTIVE COMPOUNDS AND INTERMEDIATES (Combustion Elemental Analysis)

| | | |
|---|---|---|
| 4 | Calc'd for $C_{11}H_{14}N_4O_4$: | C, 49.62; H, 5.30; N, 21.04. |
| | Found: | C, 49.54; H, 5.31; N, 21.12. |
| 5 | Calc'd for $C_{12}H_{16}N_4O_4$ + H$^+$: | HRMS 281.124980 |
| | Found: | 281.123300 |
| 6 | Calc'd for $C_{13}H_{18}N_4O_4$: | C, 53.05; H, 6.16; N, 19.04. |
| | Found: | C, 52.79; H, 6.00; N, 18.99. |
| 7 | Calc'd for $C_{14}H_{20}N_4O_4$: | C, 54.54; H, 6.54; N, 18.17. |
| | Found: | C, 54.47; H, 6.42; N, 18.16. |
| 8 | Calc'd for $C_{16}H_{16}N_4O_4 \cdot 2/3$ DMF: | C, 57.29; H, 5.52; N, 17.33. |
| | Found: | C, 57.17; H, 5.51; N, 17.35. |
| 10 | Calc'd for $C_{13}H_{17}BrN_4O_4$: | C, 41.84; H, 4.59; N, 15.01. |
| | Found: | C, 41.83; H, 4.43; N, 14.99. |
| 11 | Calc'd for $C_{16}H_{15}BrN_4O_4$: | C, 47.19; H, 3.71; N, 13.76. |
| | Found: | C, 47.02; H, 3.68; N, 13.63. |
| 12 | Calc'd for $C_{13}H_{18}N_4O_4S$: | C, 47.84; H, 5.56; N, 17.17. |
| | Found: | C, 47.98; H, 5.44; N, 16.99. |
| 13 | Calc'd for $C_{17}H_{18}N_4O_4S$: | C, 54.53; H, 4.85; N, 14.96. |
| | Found: | C, 54.41; H, 4.66; N, 14.72. |
| 20 | Calc'd for $C_{12}H_{20}N_4O_3$: | C, 53.72; H, 7.51; N, 20.88. |
| | Found: | C, 54.00; H, 7.47; N, 20.65. |
| 4 | Calc'd for $C_{12}H_{18}N_4O_3$: | C, 54.12; H, 6.81; N, 21.04. |
| | Found: | C, 54.23; H, 6.76; N, 21.04. |
| 31 | Calc'd for $C_{15}H_{22}N_4O_4$: | C, 55.89; H, 6.88; N, 17.38. |
| | Found: | C, 55.67; H, 6.94; N, 17.22. |
| 33 | Calc'd for $C_5H_8N_4O_4$: | C, 38.46; H, 5.16; N, 35.88. |
| | Found: | C, 38.22; H, 5.13; N, 35.84. |
| 34 | Calc'd for $C_7H_6N_4O_2$: | C, 47.19; H, 3.39; N, 31.45. |
| | Found: | C, 47.01; H, 3.18; N, 31.25. |
| 35 | Calc'd for $C_9H_{10}N_4O_2$: | C, 52.42; H, 4.89; N, 27.17. |
| | Found: | C, 52.20; H, 4.74; N, 27.22. |
| 36 | Calc'd for $C_{13}H_{16}N_4O_4$: | C, 53.42; H, 5.52; N, 19.17. |
| | Found: | C, 53.39; H, 5.43; N, 19.17. |
| 36a | Calc'd for $C_{11}H_{12}N_4O_4$: | C, 50.00; H, 4.58; N, 21.20. |
| | Found: | C, 49.92; H, 4.47; N, 21.26. |

TABLE 2-continued

ANALYSIS OF SELECTED INVENTIVE COMPOUNDS
AND INTERMEDIATES (Combustion Elemental Analysis)

| | | |
|---|---|---|
| 37 | Calc'd for $C_{15}H_{20}N_4O_4$: | C, 56.24; H, 6.29; N, 17.49. |
| | Found: | C, 56.04; H, 6.12; N, 17.42. |
| 37a | Calc'd for $C_{13}H_{16}N_4O_4 \cdot 4/5H_2O$: | C, 50.91; H, 5.78; N, 18.27. |
| | Found: | C, 50.64; H, 5.81; N, 18.23. |
| 38 | Calc'd for $C_{12}H_{18}N_4O_4 + H^+$: | HRMS 277.093680 |
| | Found: | 277.093800 |
| 39 | Calc'd for $C_{17}H_{22}N_4O_6$: | C, 53.96; H, 5.86; N, 14.81. |
| | Found: | C, 53.60; H, 5.73; N, 14.04. |
| 40 | Calc'd for $C_{11}H_{14}N_4O_4 \cdot 1/4H_2O$: | C, 55.34; H, 6.12; N, 23.47. |
| | Found: | C, 55.37; H, 6.02; N, 23.43. |
| 41 | Calc'd for $C_{17}H_{24}N_4O_4$: | C, 58.61; H, 6.94; H, 16.08. |
| | Found: | C, 59.22; H, 7.08; N, 15.69. |
| 41a | Calc'd for $C_{15}H_{20}N_4O_4$: | C, 56.24; H, 6.29; N, 17.49. |
| | Found: | C, 56.41; H, 6.27; N, 17.28. |
| 42 | Calc'd for $C_{13}H_{10}N_4O_4 \cdot 1/3H_2O$: | C, 60.00; H, 4.13; N, 21.53. |
| | Found: | C, 59.78; H, 3.70; N, 21.14. |
| 43 | Calc'd for $C_{19}H_{20}N_4O_4 + H^+$: | HRMS 369.156280 |
| | Found: | 369.154800 |
| 44 | Calc'd for $C_{12}H_{18}N_4O_2S + H^+$: | HRMS 283.122873 |
| | Found: | 283.121300 |
| 45 | Calc'd for $C_5H_4N_4O_2S$: | C, 32.61; H, 2.19; N, 30.42. |
| | Found: | C, 32.65; H, 2.20; N, 30.29. |
| 46 | Calc'd for $C_7H_8N_4O_2S$: | C, 39.62; H, 3.80; N, 26.40. |
| | Found: | C, 39.84; H, 3.60; N, 26.02. |
| 47 | Calc'd for $C_{11}H_{14}N_4O_4S$: | C, 44.29; H, 4.73; N, 18.78. |
| | Found: | C, 44.57; H, 4.67; N, 18.80. |
| 47a | Calc'd for $C_9H_{10}N_4O_4S + H^+$: | HRMS 271.050102 |
| | Found: | 271.050600 |
| 48 | Calc'd for $C_{13}H_{18}N_4O_4$: | C, 47.84; H, 5.56; N, 17.17. |
| | Found: | C, 47.97; H, 5.66; N, 17.08. |
| 51 | Calc'd for $C_{14}H_{20}N_2O_3 \cdot 1/2H_2O$: | C, 61.52; H, 7.74; N, 10.25. |
| | Found: | C, 61.54; H, 7.44; N, 9.77. |
| 52 | Calc'd for $C_{15}H_{18}N_2O_4 \cdot CH_3OH$: | C, 59.62; H, 6.88; N, 8.69. |
| | Found: | C, 60.61; H, 6.84; N, 8.58. |
| 52a | Calc'd for $C_{13}H_{14}N_2O_4$: | C, 59.54; H, 5.38; N, 10.68. |
| | Found: | C, 59.55; H, 5.32; N, 10.59. |

EXAMPLE 14

Synthesis of Highly Water Soluble Derivatives
Acid Hydrolysis of Compound 53

Compound 53 (1.63 g, 5.1 mmol) (prepared according to Example 9 from the parent isoquinolone) was combined with n HCl (30 mL) and was heated at boiling for 75 min. The mixture was cooled and the resulting solid which formed was filtered, washed with cold water, and dried to yield 1.5 g (quantitative conversion) of the free carboxylic acid of suitable purity for esterification (as judged by TLC).
Esterification to Form Morpholinoethyl Ester Compound 54

The carboxylic acid obtained above in this Example (1.0 g, 3.4 mmol) was dissolved in dichloromethane (25 mL) with warming and then thionyl chloride (1 mL, 13.7 mmol) was added followed by 3 drops of DMF. After a few minutes a white solid precipitated (acid chloride intermediate), but the reaction mixture was allowed to stir at room temperature overnight. The mixture was evaporated to remove excess thionyl chloride and the residue was suspended in dry acetonitrile (25 mL). To this mixture was added morpholinoethanol (1.24 mL, 10.2 mmol) and heated at 80° C. for 5 minutes. The solid suspension became clear almost immediately and after cooling, the reaction mixture was evaporated onto silica gel and loaded on a flash silica gel column and eluted with methanol—dichloromethane 5/95. The fractions of pure product were pooled and evaporated to yield an off-white residue which was dissolved in isopropyl alcohol (5 mL) and concentrated HCl (1 mL) was added. Upon concentration in vacuo, an off-white solid formed. Yield after drying 0.93 g (62%), mp 90° C. Proton NMR confirms structure assignment as the morpholino ethyl ester of Compound 53: $^1$H NMR (DMSO-$d_6$, 500 MHZ) δ7.56 and 7.15 (2s, 2H, C-5 and C-8 aromatics), 7.35 and 6.55 (2d, 2H, C-3 and C-4 aromatics), 4.37 (m, 2H, C-1' of ester), 3.92 (m, 2H, C-4 of acyl), 3.86 and 3.84 (2s, 6H, OMe's), 3.95, 3.45, 3.10 (3m, 8H, morpholino and C-2'), 2.38 (t, 2H, C-2 of acyl), 1.92 (m, 2H, C-3 of acyl)

The invention having been fully described, modifications thereof may be apparent to those of ordinary skill in the art. Such modifications are within the scope of the invention as defined by the appended claims.

The invention claimed is:

1. A compound of the formula:

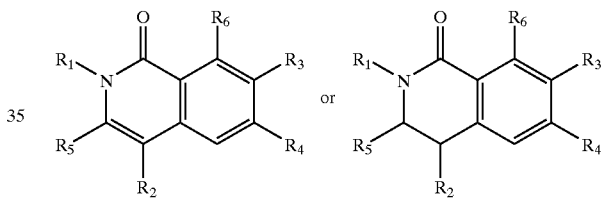

wherein
$R_1$ is a terminally substituted normal alkyl having from 1 to 7 carbon atoms, a terminally substituted alkenyl having from 2 to 7 carbon atoms, a terminally substituted ether having from 2 to 6 carbon atoms, a terminally substituted secondary amine having from 2 to 6 carbon atoms, or substituted aryl having less than 8 carbons, where the terminal group is $SO_2R$ or COOR, where R is an alkylamino, where the alkyl group has from 1 to 4 carbon atoms and the amino is $NH_2$ or a substituted amino where the substituents on the amino have 1 to 6 carbon atoms, one of which can be replaced by an oxygen atom or nitrogen atom;

$R_2$ is hydrogen, alkyl, cycloalkyl, heterocyclic alkyl, alkenyl, halogen, NO, amino, substituted amino or aralkyl having from 1 to 7 carbon atoms;

$R_3$ and $R_4$ are independently H, SH, OH, alkyl, cycloalkyl, heterocyclic alkyl, alkenyl, aryl, alkylcarboxyl, or aralkyl having from 1 to 7 carbon atoms, OH or O-alkyl having from 1 to 5 carbon atoms;

$R_5$ is H, alkyl, cycloalkyl, heterocyclic alkyl, alkenyl, aryl or aralkyl having from 1 to 7 carbon atoms, OH, or O-alkyl having from 1 to 5 carbon atoms; and $R_6$ is H, NO, amino, or substituted amino,
or a salt thereof.

2. The compound of claim 1 having the formula:

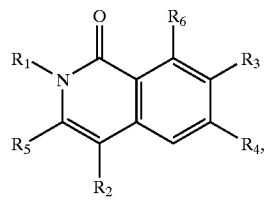

wherein
  $R_2$, is hydrogen, alkyl, cycloalkyl, heterocyclic alkyl, alkenyl, or aralkyl having from 1 to 7 carbon atoms.

3. The compound of claim 1, having the formula:

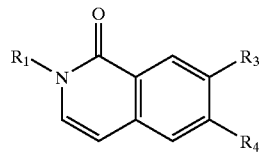

wherein
  $R_1$ is a terminally substituted normal alkyl having from 1 to 7 carbon atoms wherein said terminal group is COOR, wherein R is aminoalkyl, wherein the alkyl group has from 1 to 4 carbon atoms and wherein the substituents on the amino form an N-morpholino group; and
  each of $R_3$ and $R_4$, independently, is H, alkyl having less than 7 carbon atoms, or O-alkyl having from 1 to 5 carbon atoms.

4. The compound of claim 2, wherein $R_1$ is a terminally substituted normal alkyl having from 1 to 7 carbon atoms, wherein said terminal group and is COOR, wherein R is aminoalkyl, wherein the alkyl group has from 1 to 4 carbon atoms and the amino is a substituted amino wherein the substituents on the amino have 1 to 6 carbon atoms, one of which can be replaced by an oxygen atom or nitrogen atom.

5. The compound of claim 4, wherein $R_1$ is a terminally substituted normal alkyl having from 1 to 4 carbon atoms wherein said terminal group is COOR wherein R is aminoalkyl, wherein the alkyl group has from 1 to 4 carbon atoms; and
  each of $R_3$ and $R_4$, independently, is an O-alkyl group having from 1 to 5 carbon atoms.

6. The compound of claim 5, wherein $R_1$ is —$(CH_2)_3$COOR wherein R is an N-morpholinoethyl group, and $R_3$ and $R_4$ each are methoxy groups.

7. The compound of claim 4, wherein $R_1$ is —$(CH_2)_3$COOR wherein R is an N-morpholinoethyl group, and $R_2$ is alkyl having less than 4 carbon atoms, and each of $R_3$ and $R_4$, independently, is H, alkyl having 1 to 3 carbon atoms, phenyl, or carboxymethyl.

8. The compound of claim 1 having the formula:

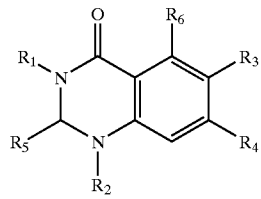

wherein
  $R_2$, is hydrogen, alkyl, cycloalkyl, heterocyclic alkyl, alkenyl, or aralkyl having from 1 to 7 carbon atoms.

9. The compound of claim 8, having the formula:

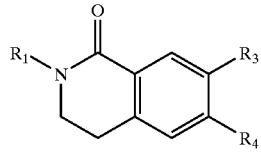

wherein
  $R_1$ is a terminally substituted normal alkyl having from 1 to 7 carbon atoms wherein said terminal group is COOR, wherein R is aminoalkyl, wherein the alkyl group has from 1 to 4 carbon atoms and wherein the substituents on the amino form an N-morpholino group; and
  each of $R_3$ and $R_4$, independently, is H, alkyl having less than 7 carbon atoms, or O-alkyl having from 1 to 5 carbon atoms.

10. The compound of claim 9, wherein $R_1$ is a terminally substituted normal alkyl having from 1 to 7 carbon atoms, wherein said terminal group and is COOR, wherein R is aminoalkyl, wherein the alkyl group has from 1 to 4 carbon atoms and the amino is a substituted amino wherein the substituents on the amino have 1 to 6 carbon atoms, one of which can be replaced by an oxygen atom or nitrogen atom.

11. The compound of claim 10, wherein $R_1$ is a terminally substituted normal alkyl having from 1 to 4 carbon atoms wherein said terminal group is COOR wherein R is aminoalkyl, wherein the alkyl group has from 1 to 4 carbon atoms; and
  each of $R_3$ and $R_4$, independently, is an O-alkyl group having from 1 to 5 carbon atoms.

12. The compound of claim 11, wherein $R_1$ is —$(CH_2)_3$COOR wherein R is an N-morpholinoethyl group, and $R_3$ and $R_4$ each are methoxy groups.

13. The compound of claim 12, wherein $R_1$ is —$(CH_2)_3$COOR wherein R is an N-morpholinoethyl group, and $R_2$ is alkyl having less than 4 carbon atoms, and each of $R_3$ and $R_4$, independently, is H, alkyl having 1 to 3 carbon atoms, phenyl, or carboxymethyl.

14. A method for treating inflammation or fibrosis by inhibiting TNF-α activity in a host comprising administering to the host a therapeutically effective amount of the compound of claim 1 in a physiologically acceptable carrier.

* * * * *

UNITED STATES PATENT AND TRADEMARK OFFICE
CERTIFICATE OF CORRECTION

PATENT NO. : 6,562,819 B2
DATED : May 13, 2003
INVENTOR(S) : Carson et al.

It is certified that error appears in the above-identified patent and that said Letters Patent is hereby corrected as shown below:

Column 1,
Line 35, delete "Dressier" and insert -- Dressler --, therefor.
Line 41, delete "deramide" and insert -- ceramide --, therefor.

Column 2,
Line 64, delete "UW" and insert -- UV --, therefor.

Column 24,
Line 65, delete "are-synthesized" and insert -- are synthesized --, therefor.

Columns 25-26,
Scheme II, line 3, delete "to this e n" and insert -- to this end --, therefor.

Column 25,
Line 45, delete "fo" and insert -- of --, therefor.

Column 26,
Line 64, delete "and," before "preferably".

Column 27,
Scheme III, line 33, after "47a, $R_1$ = $(CH_2)_3COOEt$ $R_2$ =" delete "$C_3H_7$" and insert -- Me --, therefor.
Line 48, delete "10" after "these".

Column 28,
Line 21, delete "R" and insert -- R' --, therefor.

Column 29,
Line 27, delete "are" after "preferably".

Column 30,
Line 16, delete "ceramidemediated" and insert -- ceramide-mediated --, therefor.

UNITED STATES PATENT AND TRADEMARK OFFICE
CERTIFICATE OF CORRECTION

PATENT NO. : 6,562,819 B2
DATED : May 13, 2003
INVENTOR(S) : Carson et al.

It is certified that error appears in the above-identified patent and that said Letters Patent is hereby corrected as shown below:

Column 36,
Line 18, delete "$\mu$" before "Aliquots".
Line 22, delete "$\mu$" before "Aldrich".
Line 29, delete "$\mu$g/ml." and insert -- pg/ml. --, therefor.
Line 64, delete "$\mu$" before "Alkylation".

Signed and Sealed this

Twelfth Day of August, 2003

JAMES E. ROGAN
*Director of the United States Patent and Trademark Office*